US011414482B2

United States Patent
Li et al.

(10) Patent No.: US 11,414,482 B2
(45) Date of Patent: Aug. 16, 2022

(54) ANTI-SECRETOGRANIN III (SCG3) ANTIBODIES AND USES THEREOF

(71) Applicant: UNIVERSITY OF MIAMI, Miami, FL (US)

(72) Inventors: Wei Li, Miami, FL (US); Michelle E. Leblanc, Millbury, MA (US); Weiwen Wang, Miami, FL (US); Philip J. Rosenfeld, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 314 days.

(21) Appl. No.: 16/347,668

(22) PCT Filed: Nov. 6, 2017

(86) PCT No.: PCT/US2017/060189
§ 371 (c)(1),
(2) Date: May 6, 2019

(87) PCT Pub. No.: WO2018/089305
PCT Pub. Date: May 17, 2018

(65) Prior Publication Data
US 2019/0315848 A1   Oct. 17, 2019

Related U.S. Application Data

(60) Provisional application No. 62/419,195, filed on Nov. 8, 2016.

(51) Int. Cl.
*C07K 16/22* (2006.01)
*A61P 27/02* (2006.01)
*A61K 9/00* (2006.01)

(52) U.S. Cl.
CPC ............ *C07K 16/22* (2013.01); *A61K 9/0019* (2013.01); *A61K 9/0048* (2013.01); *A61P 27/02* (2018.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,331,647 A | 5/1982 | Goldenberg |
| 4,411,993 A | 10/1983 | Gillis |
| 4,496,689 A | 1/1985 | Mitra |
| 4,543,439 A | 9/1985 | Frackelton et al. |
| RE32,011 E | 10/1985 | Zimmerman et al. |
| 4,640,835 A | 2/1987 | Shimizu et al. |
| 4,670,417 A | 6/1987 | Iwasaki et al. |
| 4,791,192 A | 12/1988 | Nakagawa et al. |
| 4,902,614 A | 2/1990 | Wakabayashi et al. |
| 5,399,363 A | 3/1995 | Liversidge et al. |
| 5,466,468 A | 11/1995 | Schneider et al. |
| 6,133,426 A | 10/2000 | Gonzalez et al. |
| 10,106,787 B2 | 10/2018 | Li |
| 2004/0146888 A1 | 7/2004 | Paszty et al. |
| 2019/0204302 A1 | 7/2019 | Li |

FOREIGN PATENT DOCUMENTS

| | | |
|---|---|---|
| WO | 2006/010532 A1 | 2/2006 |
| WO | 2006/119107 A2 | 11/2006 |
| WO | 2010/078526 A1 | 7/2010 |
| WO | 2014/014819 A2 | 1/2014 |
| WO | 2015/184207 A1 | 12/2015 |

OTHER PUBLICATIONS

Rudikoff et al., (PNAS 79: 1979-1983, 1982).*
Stridsberg et al (J Anat 212: 229-234, 2008).*
Martins-Green et al., An assay system for in vitro detection of permeability in human "endothelium", Methods Enzymol., 443:137-53 (2008).
Matei et al., PDGF BB induces VEGF secretion in ovarian cancer, Cancer Biol. Ther., 6:1951-9 (2007).
Mullis et al., PCR: The Polymerase Chain Reaction, (1994).
Mylonas et al., Comparison of Dexamethasone Intravitreal Implant with Conventional Triamcinolone in Patients with Postoperative Cystoid Macular Edema, Curr. Eye. Res., 42:648-652 (2016).
Nisonoff et al., Separation of Univalent Fragments from the Bivalent Rabbit Antidody Molecule by Reduction of Disulfide Bonds, Arch. Biochem. Biophys., 89:230-244 (1960).
Oliver et al., An endothelial growth factor involved in rat renal development, J. Clin. Invest., 102:1208-19 (1998).
Patten et al., Applications of DNA Shuffling to Pharmaceuticals and Vaccines, Curr. Opin. Biotechnol., 8:724-733 (1997).
Peerschke et al., Expression of gC1q-R/p33 and its major ligands in human atherosclerotic lesions, Mol. Immunol., 41:759-66 (2004).
Picksley et al., DNA Cloning 2: Expression Systems, Oxford University Press, article, Production of monoclonal antibodies against proteins expressed in *E. coli*, 93 (1995).
Pinheiro-Costa et al., Switch from intravitreal ranibizumab to bevacizumab for the treatment of neovascular age-related macular degeneration: clinical comparison, Ophthalmologica., 232:149-55 (2014).
Pluckthun et al., Expression of Functional Anitbody Fv and Fab Fragments in *Escherichia coli*, Methods EnzymoL., 178:497-515 (1989).
Poor et al., Reliability of the mouse model of choroidal neovascularization induced by laser photocoagulation, Invest. Ophthalmol. Vis. Sci., 55:6525-34 (2014).

(Continued)

*Primary Examiner* — Daniel E Kolker
*Assistant Examiner* — Aditi Dutt
(74) *Attorney, Agent, or Firm* — Marshall, Gerstein & Borun LLP

(57) ABSTRACT

Antibodies specific for secretogranin III (Scg3) are disclosed. Methods of using the antibodies, antigen-binding fragments thereof, or pharmaceutical compositions comprising the same in the treatment of diseases such as diabetic retinopathy, neovascular age-related macular degeneration, retinopathy of prematurity, and cancer, are also disclosed.

8 Claims, 13 Drawing Sheets

Specification includes a Sequence Listing.

(56) References Cited

OTHER PUBLICATIONS

Porter, The Hydrolysis of Rabbit ?-Globulin and Antibodies with Crystalline Papain, Biochem. J., 73:119-126 (1959).
Rask-Madsen et al., Vascular complications of diabetes: mechanisms of injury and protective factors, Cell. Metab., 17:20-33(2013).
Robinson et al., The splice variants of vascular endothelial growth factor (VEGF) and their receptors, J. Cell. Sci., 114:853-65 (2001).
Rozek et al., Mass spectrometry identification of granins and other proteins secreted by neuroblastoma cells, Tumour Biol., 34:1773-1781 (2013).
Sanger et al., DNA Sequencing with Chain-Terminating Inhibitors, PNAS, 74:5463-5467 (1997).
Sankar et al., Anti-vascular endothelial growth factor (VEGF) drugs for treatment of retinopathy of prematurity, Cochrane Database Syst. Rev., 2:CD009734 (2016).
Scatchard et al., The Attractions of Proteins for Small Molecules and Ions, Ann. N.Y. Acad. Sci., 51:660-672 (1949).
Scheppke et al., Retinal vascular permeability suppression by topical application of a novel VEGFR2/Src kinase inhibitor in mice and rabbits, J. Clin. Invest., 118:2337-46 (2008).
Schwartz et al., Emerging drugs for diabetic macular edema, Expert Opin. Emerg. Drugs, 19:397-405 (2014).
Seghezzi et al., Fibroblast growth factor-2 (FGF-2) induces vascular endothelial growth factor (VEGF) expression in the endothelial cells of forming capillaries: an autocrine mechanism contributing to angiogenesis, J. Cell. Biol., 141:1659-73 (1998).
Shalaby et al., Failure of blood-island formation and vasculogenesis in Flk-1-deficient mice, Nature, 376:62-66 (1995).
Shao et al., Neovascular Age-Related Macular Degeneration, Dev. Ophthalmol., 55:125-36 (2016).
Stahl et al., The mouse retina as an angiogenesis model, Invest Ophthalmol Vis. Sci., 51:2813-26 (2010).
Taupenot et al., The chromogranin-secretogranin family, N. Engl. J. Med., 348:1134-49 (2003).
Thompson et al., Affinity Maturation of a High-Affinity Human Monoclonal Antibody Against the Third Hypervariable Loop of Human Immunodeficiency Virus: Use of Phage Display to Improve Affinity and Broaden Strain Reactivity, J. Mol. Biol., 256:77-88 (1996).
Toissel, ASHP Handbook on Injectable Drugs, 4th ed., 622-630 (1986).
Valk et al., CTLA-4 trafficking and surface expression, Trends Immunol., 29:272-9 (2008).
Vaughan et al., Human antibodies by design, Nature Biotechnology, 16:535-539 (1998).
Vogel et al., Apolipoprotein E: a potent inhibitor of endothelial and tumor cell proliferation, Journal of Cellular Biochemistry, 54:299-308 (1994).
Wang et al., A mutation in the insulin 2 gene induces diabetes with severe pancreatic beta-cell dysfunction in the Mody mouse, J. Clin. Invest., 103:27-37 (1999).
Wang et al., Induction of vascular endothelial growth factor expression in endothelial cells by platelet-derived growth factor through the activation of phosphatidylinositol 3-kinase, Cancer research, 59:1464-72 (1999).
Wang et al., The oncoprotein HBXIP up-regulates SCG3 through modulating E2F1 and miR-509-3p in hepatoma cells, Cancer Letters, 352:169-178 (2014).
Ward et al., Binding activities of a repertoire of single immunoglobulin variable domains secreted from *Escherichia coli*, Nature, 341:544-546 (1989).
Wolff et al., Monoclonal Antibody Homodimers: Enhanced Antitumor Activity in Nude Mice, Cancer Res., 53:2560-2565 (1993).
Yang et al., CDR Walking Mutagenesis for the Affinity Maturation of a Potent Human Anti-HIV-1 Antibody into the Picomolar Range, J. Mol. Biol., 254:392-403 (1995).

Zhong et al., Activation of endoplasmic reticulum stress by hyperglycemia is essential for Müller cell-derived inflammatory cytokine production in diabetes, Diabetes, 61:492-504 (2012).
Portela-Gomes et al., Secretogranin III in human neuroendocrine tumoursA comparative immunohistochemical study with chromogranins A and Band secretogranin II, Reg. Pep., 165(1):30-35 (2010).
Sakai et al., Immunocytochemical localization of secretogranin III in the endocrine pancreas of male rats, Arch. His. Cyt . . . , 67(1):57-64 (2004).
Baines et al., Purification of Immunoglobulin G (IgG), in Methods in Molecular Biology, 10:79-104 (1992).
Banker et al., Pharmaceutics and Pharmacy Practice, J.B. Lippincott Co., Philadelphia. Pa., 238-250 (1982).
Beharry et al., Pharmacologic interventions for the prevention and treatment of retinopathy of prematurity, Semin Perinatol., 40:189-202 (2016).
Birch et al., Randomized trial of ciliary neurotrophic factor delivered by encapsulated cell intraocular implants for retinitis pigmentosa, Am. J. Ophthalmol., 156:283-292 (2013).
Bird et al., Single-chain antigen-binding proteins, Science, 242:423-426 (1988).
Caberoy et al., Can phage display be used as a tool to functionally identify endogenous eat-me signals in phagocytosis?, J. Biomol. Screen., 14:653-61 (2009).
Caberoy et al., Efficient identification of tubby-binding proteins by an improved system of T7 phage display, J. Mol. Recognit., 23:74-83 (2010).
Caberoy et al., Tubby and tubby-like protein 1 are new MerTK ligands for phagocytosis, EMBO. J., 29:3898-910 (2010).
Cao et al., A subretinal matrigel rat choroidal neovascularization (CNV) model and inhibition of CNV and associated inflammation and fibrosis by VEGF trap, Invest Ophthalmol Vis. Sci., 51:6009-17 (2010).
Carmeliet, Angiogenesis in health and disease, Nature Medicine, 9:654-660 (2003).
Chan et al., Attenuation of choroidal neovascularization by histone deacetylase inhibitor, PLoS One, 10:e0120587 (2015).
Connor et al., Quantification of oxygen-induced retinopathy in the mouse: a model of vessel loss, vessel regrowth and pathological angiogenesis, Nat. Protoc., 4:1565-73 (2009).
Coppinger et al., Characterization of the proteins released from activated platelets leads to localization of novel platelet proteins in human atherosclerotic lesions, Blood, 103:2096-104 (2004).
Davidson et al., The impact of pediatric vision disorders in adulthood, Pediatrics., 127:334-9 (2011).
Dedania et al., Current perspectives on ranibizumab, Clin. Ophthalmol., 9:533-42 (2015).
Dowling et al., Proteomic analysis of conditioned media from glucose responsive and glucose non-responsive phenotypes reveals a panel of secreted proteins associated with beta cell dysfunction, Electrophoresis, 29:4141-9 (2008).
Estep et al., High throughput solution-based measurement of antibody-antigen affinity and epitope binning, MAbs. 5:270-278 (2013).
Ferrara et al., Heterozygous embryonic lethality induced by targeted inactivation of the VEGF gene, Nature, 380:439-442 (1996).
Fieger et al., Endoglycan, a member of the CD34 family, functions as an L-selectin ligand through modification with tyrosine sulfation and sialyl Lewis x, J. Biol. Chem., 278:27390-8 (2003).
Fong et al., Role of the Flt-1 receptor tyrosine kinase in regulating the assembly of vascular endothelium, Nature, 376:66-70 (1995).
Forbes et al., Mechanisms of diabetic complications, Physiol. Rev., 93:137-88 (2013).
Freshney R.I., Animal Cell Culture: A Practical Approach, Biomed. Edu. 15(1):53 (1987).
Guo et al., ABCF1 extrinsically regulates retinal pigment epithelial cell phagocytosis, Mol. Biol. Cell., 26:2311-20 (2015).
Harlow et al., Antibodies: A Laboratory Manual, Cold Spring Harbor Laboratory Press (1988).
Harris RJ., Processing of C-terminal lysine and arginine residues of proteins isolated from mammalian cell culture, Journal of Chromatography, 705:129-134 (1995).
Helle et al., Chromogranin A: a paradoxical player in angiogenesis and vascular biology, Cell. Mol. Life. Sci., 72:339-48 (2015).

(56) References Cited

OTHER PUBLICATIONS

Helle KB., The granin family of uniquely acidic proteins of the diffuse neuroendocrine system: comparative and functional aspects, Biol. Rev. Camb. Philos. Soc., 79:769-94 (2004).

Hosaka et a., Secretogranin III: a bridge between core hormone aggregates and the secretory granule membrane, Endocrine J., 57:275-86 (2010).

Houtman, FASEB Breakthroughs in Bioscience, 1-17 (2010).

Huston et al., Protein engineering of antibody binding sites: recovery of specific activity in an anti-digoxin single-chain Fv analogue produced in *Escherichia coli*, Proc. Natl. Acad. Sci., 85:5879-5883 (1988).

International Preliminary Report on Patentability for corresponding International Application No. PCT/US2017/060189, dated May 23, 2019.

International Search Report and Written Opinion for corresponding International Application No. PCT/US2017/060189, dated Mar. 28, 2018.

Izumoto et al., Hepatoma-derived growth factor belongs to a gene family in mice showing significant homology in the amino terminus, Biochem Biophys. Res. Conimun., 238:26-32 (1997).

Jeganathan VS., Anti-angiogenesis drugs in diabetic retinopathy, Current pharmaceutical biotechnology, 12:369-72 (2011).

Kaipainen et al., Expression of the fms-like tyrosine kinase 4 gene becomes restricted to lymphatic endothelium during development, Proc Natl Acad Sci U. S. A., 92:3566-70 (1995).

Kim et al., Identification of Hnrph3 as an autoantigen for acute anterior uveitis, Clin. Immunol., 138:60-6 (2011).

Kingsley et al., Genetic ablation of a mouse gene expressed specifically in brain, EMBO. J., 9:395-399 (1990).

Kohler et al., Continuous cultures of fused cells secreting antibody of predefined specificity, Nature, 256:495-7 (1975).

Kramer et al., The gapped duplex DNA approach to oligonucleotide-directed mutation construction, Nucleic Acids Res., 12:9441-56 (1984).

Kunkel et al., Rapid and efficient site-specific mutagenesis without phenotypic selection, Methods in Enzymol., 154:367-82 (1987).

Kunkel TA., Rapid and efficient site-specific mutagenesis without phenotypic selection, Proc. Natl. Acad. Sci., U. S. A., 82:488-92 (1985).

Kweider et al., Interplay between vascular endothelial growth factor (VEGF) and nuclear factor erythroid 2-related factor-2 (Nrf2): implications for preeclampsia, J. Biol. Chem., 286:42863-72 (2011).

Larrick et al., PCR amplification of antibody genes, Methods: A Companion to Methods in Enzymology, 2:106-110 (1991).

Leblanc et al., Hepatoma-derived growth factor-related protein-3 is a novel angiogenic factor, PLoS One, 10:e0127904 (2015).

Leblanc et al., The regulatory role of hepatoma-derived growth factor as an angiogenic factor in the eye, Mol. Vis., 22:374-86 (2016).

Lepore et al., Intravitreal bevacizumab versus laser treatment in type 1 retinopathy of prematurity: report on fluorescein angiographic findings, Ophthalmology, 121:2212-2219 (2014).

Low et al., Mimicking Somatic Hypermutation: Affinity Maturation of Antibodies Displayed on Bacteriophage using a Bacterial Mutator Strain, J. Mol. Biol., 250:350-368 (1996).

Maity et al., Epidermal growth factor receptor transcriptionally up-regulates vascular endothelial growth factor expression in human glioblastoma cells via a pathway involving phosphatidylinositol 3′-kinase and distinct from that induced by hypoxia, Cancer research, 60:5879-86 (2000).

Maniatis et al., Molecular Cloning, A Laboratory Manual, 2nd ed., Cold Spring Harbor Laboratory, New York, (1989).

Marks et al., By-Passing Immunization: Building High Affinity Human Antibodies by Chain Shuffling, Bio/Technology, 10:779-783 (1992).

\* cited by examiner

Figure 8A	Figure 8B	Figure 8C
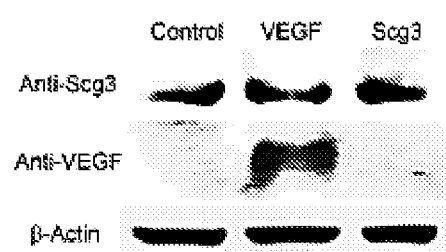 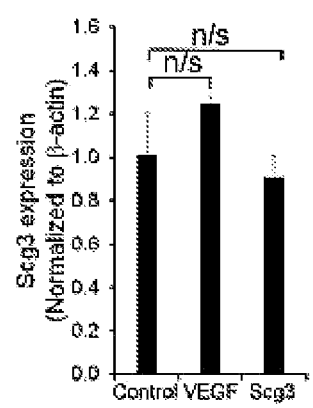 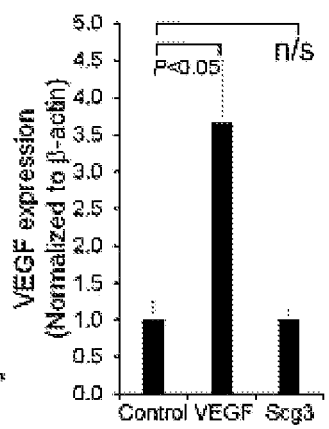
Figure 9A
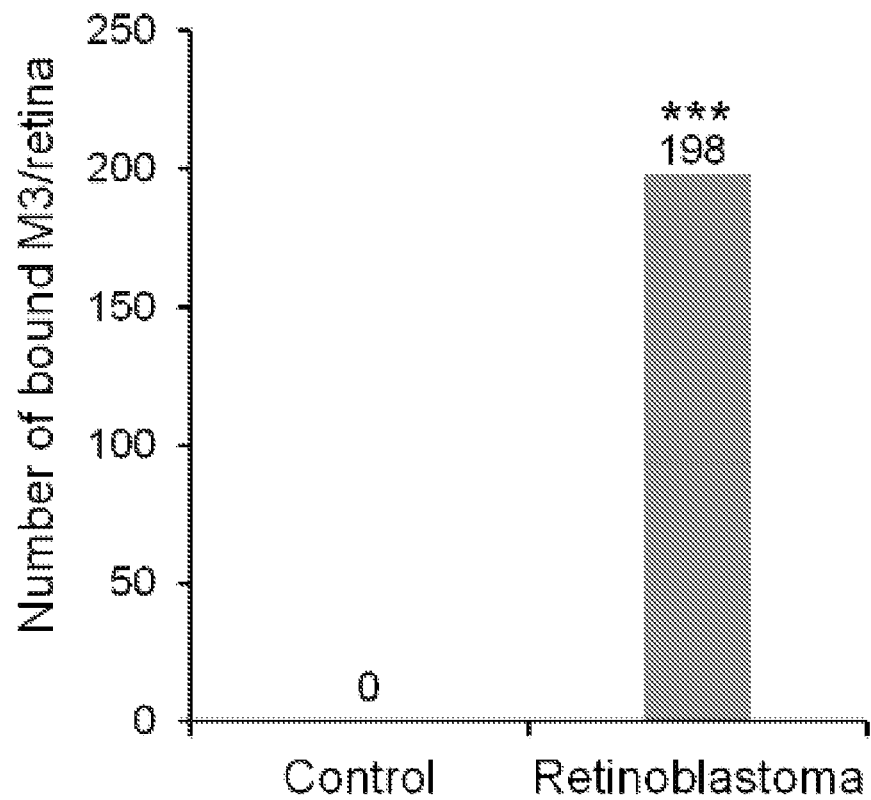

ANTI-SECRETOGRANIN III (SCG3) ANTIBODIES AND USES THEREOF

CROSS-REFERENCE TO RELATED APPLICATIONS AND INCORPORATION BY REFERENCE OF MATERIAL SUBMITTED ELECTRONICALLY

This application is a national phase of PCT/US2017/060189, filed Nov. 6, 2017, which claims priority to U.S. Provisional Patent Application No. 62/419,195 filed Nov. 8, 2016, the disclosure of which is hereby incorporated by reference in its entirety.

STATEMENT OF GOVERNMENT INTEREST

This invention was made with government support under #R01GM094449 awarded by the National Institutes of Health. The government has certain rights in the invention.

This application contains, as a separate part of the disclosure, a Sequence Listing in computer-readable form which is incorporated by reference in its entirety and identified as follows: Filename: 51085A_Seqlisting.txt; Size 23,955 bytes; Created: May 3, 2019.

FIELD OF THE INVENTION

The disclosure generally relates to anti-secretogranin III antibodies and uses thereof.

BACKGROUND

Diabetic retinopathy (DR) and age-related macular degeneration (AMD) are major causes of vision loss. DR affects about 93 million people world-wide, including about 28 million with vision-threatening diabetic macular edema (DME) and proliferative diabetic retinopathy (PDR). DR in early stages is characterized by apoptosis of endothelial cells (ECs) and pericytes, vascular leakage and leukocyte adhesion, and may progress towards acellular capillaries, microaneurisms, retinal vein occlusion, DME and PDR. AMD has two clinical forms: dry (atrophic) and wet (neovascular or exudative). Neovascular AMD (nAMD) with choroidal neovascularization (CNV) afflicts 10-20% of individuals with the disease, but accounts for about 90% of all cases with severe vision loss from the disease.

Angiogenic factors play an important role in the pathogenesis of DME with retinal vascular leakage, PDR with retinal neovascularization, and nAMD. The approval of vascular endothelial growth factor (VEGF) inhibitors, including LUCENTIS (ranibizumab) and EYLEA (aflibercept), was a major breakthrough in DR and nAMD therapy (Schwartz et al. *Expert Opin Emerg Drugs.* 2014; 19(3): 397-405; Shao et al. *Dev Ophthalmol.* 2016; 55:125-36). However, anti-VEGF therapies have limited efficacies and can improve vision only in less than 50% of DR and nAMD cases (Dedania and Bakri *Clin Ophthalmol.* 2015; 9:533-42), suggesting that other angiogenic factors may be involved in the pathogenesis of these diseases. Due to limited options, patients with a poor response to one anti-VEGF drug are often switched to another VEGF inhibitor (Pinheiro-Costa et al. *Ophthalmologica.* 2014; 232(3):149-55), despite their similar mechanisms of action. Additionally, most angiogenic factors regulate neovascularization in both normal and diseased vessels, so therapies against these targets may thus affect normal vessels and cells with detrimental effects. Consequently, all VEGF inhibitors are approved for AMD therapy only via intravitreal administration. Despite the low rate of side effects for a single intravitreal injection, repetitive intravitreal injections may cause adverse effects in the eye, such as endophthalmitis, retinal detachment, increased intraocular pressure and cataracts. The prevention of DME, PDR and nAMD in early stage or high-risk subjects requires repeated intravitreal injections of VEGF inhibitors. Therefore, anti-VEGF therapy is not approved for the prevention of DME, PDR or nAMD. To resolve the problems of existing treatments, new therapies for DR and AMD via topical eye drops or with long-lasting duration are needed to avoid or reduce the frequency of intravitreal injection.

Anti-VEGF therapy has also been evaluated for use in treating retinopathy of prematurity (ROP), which is the most common cause of blindness in children. ROP affects 14,000 to 16,000 pre-term infants each year in the U.S., with similar high rates in other countries. ROP is characterized by pathological retinal neovascularization (NV) and may progress toward partial or complete retinal detachment with severe visual impairment and even blindness. Infants with ROP are considered to be at higher risk for developing other ocular diseases in adulthood, such as retinal detachment, myopia, strabismus, amblyopia and glaucoma (Davidson and Quinn, *Pediatrics.* 2011; 127(2):334-9). ROP is currently treated with laser therapy or cryotherapy (Hellstrom et al., *Lancet.* 2016; 40(3):189-202). Unfortunately, both treatments destroy the peripheral vision to save the central vision and do not address the underlying cause of ROP. Several clinical trials with VEGF inhibitors showed limited efficacy for ROP (Sankar et al., *Cochrane Database Syst. Rev.* 2016; 2:CD009734), and the safety of anti-VEGF therapy for ROP is a major concern. VEGF is crucial to vascular morphogenesis and retinal development at embryonic and neonatal stages. Mice with homozygous deletion of either VEGF receptor 1 or 2 die in the uterus (Fong et al., *Nature.* 1995; 376(6535):66-70; Shalaby et al., *Nature.* 1995; 376(6535): 62-6). Similarly, mice with the deletion of a single VEGF allele are embryonically lethal (Ferrara et al., *Nature.* 1996; 380(6573); 439-42). Off-label use of VEGF inhibitors to treat ROP was also associated with significant adverse outcomes (Beharry et al, *Semin Perinatol.* 2016; 40(3)189-202). These findings raise a significant safety concern regarding anti-VEGF therapy in preterm infants. Consequently, owing to the limited efficacy and safety, VEGF inhibitors are not approved for ROP therapy, more than a decade after their approval for nAMD, and there is currently no FDA-approved drug for ROP.

Developing new anti-angiogenic therapies with high efficacy, VEGF-independent mechanisms, and flexible administration routes are priorities for DR, nAMD, and ROP, and can be effective for treating other diseases, including cancer.

SUMMARY

The disclosure is directed to antibodies, and fragments and derivatives thereof, that specifically bind to secretogranin III (Scg3) and their use in treating diseases including diabetic retinopathy (DR), neovascular age-related macular degeneration (nAMD), retinopathy of prematurity (ROP), and cancer.

In one aspect, the disclosure provides an antibody or antigen-binding fragment thereof that cross-blocks a reference antibody from binding to Scg3, wherein the reference antibody is selected from the group consisting of an antibody comprising complementarity determining regions (CDRs) of SEQ ID NOs: 3-8; an antibody comprising CDRs of SEQ ID NOs: 11-16; an antibody comprising CDRs of SEQ ID NOs: 19-24; an antibody comprising CDRs of SEQ ID NOs: 27, 4, 28, 22, 29, and 24; an antibody comprising CDRs of SEQ ID NOs: 27, 4, 28, 32, 29, and 24; and an antibody comprising CDRs of SEQ ID NOs: 3, 4, 28, 22, 29, and 24. For example, the reference antibody is selected from the group consisting of an antibody comprising a heavy chain variable region comprising SEQ ID NO: 1 and a light chain variable region comprising SEQ ID NO: 2; an antibody comprising a heavy chain variable region comprising SEQ ID NO: 9 and a light chain variable region comprising SEQ ID NO: 10; an antibody comprising a heavy chain variable region comprising SEQ ID NO: 17 and a light chain variable region comprising SEQ ID NO: 18; an antibody comprising a heavy chain variable region comprising SEQ ID NO: 25 and a light chain variable region comprising SEQ ID NO: 26; an antibody comprising a heavy chain variable region comprising SEQ ID NO: 30 and a light chain variable region comprising SEQ ID NO: 31; an antibody comprising a heavy chain variable region comprising SEQ ID NO: 38 and a light chain variable region comprising SEQ ID NO: 33; and an antibody comprising a heavy chain variable region comprising SEQ ID NO: 34 and a light chain variable region comprising SEQ ID NO: 35.

In another aspect, the disclosure provides an antibody or antigen-binding fragment thereof that binds secretogranin III and comprises CDR-H1, CDR-H2, CDR-H3, CDR-L1, CDR-L2, and CDR-L3, wherein (a) CDR-H1 comprises an amino acid sequence selected from the group consisting of SEQ ID NOs: 3, 11, 19, and 27; (b) CDR-H2 comprises an amino acid sequence selected from the group consisting of SEQ ID NOs: 4, 12, and 20; (c) CDR-H3 comprises an amino acid sequence selected from the group consisting of SEQ ID NOs: 5, 13, 21, and 28; (d) CDR-L1 comprises an amino acid sequence selected from the group consisting of SEQ ID NOs: 6, 14, 22, and 32; (e) CDR-L2 comprises an amino acid sequence selected from the group consisting of SEQ ID NOs: 7, 15, 23, and 29; and (f) CDR-L3 comprises an amino acid sequence selected from the group consisting of SEQ ID NOs: 8, 16, and 24. For example, the antibody or antigen binding fragment thereof comprises (a) CDR-H1 comprising the amino acid sequence set forth in SEQ ID NO: 3; (b) CDR-H2 comprising the amino acid sequence set forth in SEQ ID NO: 4; (c) CDR-H3 comprising the amino acid sequence set forth in SEQ ID NO: 5; (d) CDR-L1 comprising the amino acid sequence set forth in SEQ ID NO: 6; (e) CDR-L2 comprising the amino acid sequence set forth in SEQ ID NO: 7; and (f) CDR-L3 comprising the amino acid sequence set forth in SEQ ID NO: 8. In another example, the antibody or antigen binding fragment thereof comprises (a) CDR-H1 comprising the amino acid sequence set forth in SEQ ID NO: 11; (b) CDR-H2 comprising the amino acid sequence set forth in SEQ ID NO: 12; (c) CDR-H3 comprising the amino acid sequence set forth in SEQ ID NO: 13; (d) CDR-L1 comprising the amino acid sequence set forth in SEQ ID NO: 14; (e) CDR-L2 comprising the amino acid sequence set forth in SEQ ID NO: 15; and (f) CDR-L3 comprising the amino acid sequence set forth in SEQ ID NO: 16. In still another example, the antibody or antigen binding fragment thereof comprises (a) CDR-H1 comprising the amino acid sequence set forth in SEQ ID NO: 19; (b) CDR-H2 comprising the amino acid sequence set forth in SEQ ID NO: 20; (c) CDR-H3 comprising the amino acid sequence set forth in SEQ ID NO: 21; (d) CDR-L1 comprising the amino acid sequence set forth in SEQ ID NO: 22; (e) CDR-L2 comprising the amino acid sequence set forth in SEQ ID NO: 23; and (f) CDR-L3 comprising the amino acid sequence set forth in SEQ ID NO: 24. In one example, the antibody or antigen binding fragment thereof comprises (a) CDR-H1 comprising the amino acid sequence set forth in SEQ ID NO: 27; (b) CDR-H2 comprising the amino acid sequence set forth in SEQ ID NO: 4; (c) CDR-H3 comprising the amino acid sequence set forth in SEQ ID NO: 28; (d) CDR-L1 comprising the amino acid sequence set forth in SEQ ID NO: 22; (e) CDR-L2 comprising the amino acid sequence set forth in SEQ ID NO: 29; and (f) CDR-L3 comprising the amino acid sequence set forth in SEQ ID NO: 24. In another example, the antibody or antigen binding fragment thereof comprises (a) CDR-H1 comprising the amino acid sequence set forth in SEQ ID NO: 27; (b) CDR-H2 comprising the amino acid sequence set forth in SEQ ID NO: 4; (c) CDR-H3 comprising the amino acid sequence set forth in SEQ ID NO: 28; (d) CDR-L1 comprising the amino acid sequence set forth in SEQ ID NO: 32; (e) CDR-L2 comprising the amino acid sequence set forth in SEQ ID NO: 29; and (f) CDR-L3 comprising the amino acid sequence set forth in SEQ ID NO: 24. In still another example, the antibody or antigen binding fragment thereof comprises (a) CDR-H1 comprising the amino acid sequence set forth in SEQ ID NO: 3; (b) CDR-H2 comprising the amino acid sequence set forth in SEQ ID NO: 4; (c) CDR-H3 comprising the amino acid sequence set forth in SEQ ID NO: 28; (d) CDR-L1 comprising the amino acid sequence set forth in SEQ ID NO: 22; (e) CDR-L2 comprising the amino acid sequence set forth in SEQ ID NO: 29; and (f) CDR-L3 comprising the amino acid sequence set forth in SEQ ID NO: 24.

In another aspect, the disclosure provides an antibody or antigen-binding fragment thereof that binds secretogranin III and comprises a heavy chain variable region comprising SEQ ID NO: 1, 9, 17, 25, 30, 38, or 34 and a light chain variable region comprising SEQ ID NO: 2, 10, 18, 26, 31, 33, or 35. For example, the antibody or antigen-binding fragment thereof comprises a heavy chain variable region comprising SEQ ID NO: 1 and a light chain variable region comprising SEQ ID NO: 2. In another example, the antibody or antigen-binding fragment thereof comprises a heavy chain variable region comprising SEQ ID NO: 9 and a light chain variable region comprising SEQ ID NO: 10. In still another example, the antibody or antigen-binding fragment thereof comprises a heavy chain variable region comprising SEQ ID NO: 17 and a light chain variable region comprising SEQ ID NO: 18. In one example, the antibody or antigen-binding fragment thereof comprises a heavy chain variable region comprising SEQ ID NO: 25 and a light chain variable region comprising SEQ ID NO: 26. In another example, the antibody or antigen-binding fragment thereof comprises a heavy chain variable region comprising SEQ ID NO: 30 and a light chain variable region comprising SEQ ID NO: 31. In still another example, the antibody or antigen-binding fragment thereof comprises a heavy chain variable region comprising SEQ ID NO: 38 and a light chain variable region comprising SEQ ID NO: 33. In another example, the antibody or antigen-binding fragment thereof comprises a heavy chain variable region comprising SEQ ID NO: 34 and a light chain variable region comprising SEQ ID NO: 35. In one aspect, the disclosure provides an antibody or antigen-binding fragment thereof that binds secretogranin III and comprises a heavy chain variable domain comprising an amino acid sequence at least 90% identical to SEQ ID NO: 1, 9, 17, 25, 30, 38, or 34, and comprising a light chain variable region comprising an amino acid sequence at least 90% identical to SEQ ID NO: 2, 10, 18, 26, 31, 33, or 35.

In another aspect, the disclosure provides a nucleic acid encoding an antibody or antigen-binding fragment described herein. In one aspect, the disclosure provides an expression vector comprising a nucleic acid encoding an antibody or antigen-binding fragment described herein and a host cell transformed with said expression vector.

In one aspect, the disclosure provides a pharmaceutical composition comprising an antibody or antigen-binding fragment described herein and a physiologically acceptable diluent, excipient or carrier. In another aspect, the disclosure provides a kit comprising an antibody or antigen-binding fragment thereof described herein or pharmaceutical composition comprising said antibody or antigen-binding fragment thereof.

The disclosure also provides medical uses for the antibodies and antigen-binding fragments described herein. In one aspect, a method of treating nAMD in a subject in need thereof comprising administering a therapeutically effective amount of an antibody, antigen-binding fragment thereof, or pharmaceutical composition described herein. For example, the antibody, antigen-binding fragment thereof, or pharmaceutical composition is administered in an amount effective to inhibit CNV and/or polypoidal choroidal vasculopathy (PCV), the latter of which is considered to be a variant of nAMD.

In one aspect, a method of treating diabetic retinopathy in a subject in need thereof is provided, wherein the method comprises administering a therapeutically effective amount of the antibody, antigen-binding fragment thereof or pharmaceutical composition described herein. In another aspect, a method of treating retinopathy of prematurity in a subject in need thereof is provided, wherein the method comprises administering a therapeutically effective amount of the antibody, antigen-binding fragment thereof or pharmaceutical composition described herein. For example, the antibody, antigen-binding fragment thereof, or pharmaceutical composition is administered in an amount effective to decrease retinal vascular leakage and/or retinal neovascularization and/or choroidal neovascularization.

In one aspect, a method of treating cancer in a subject in need thereof is provided, the method comprising administering a therapeutically effective amount of the antibody, antigen-binding fragment thereof or pharmaceutical composition described herein. For example, the antibody, antigen-binding fragment thereof, or pharmaceutical composition is administered in an amount effective to reduce tumor burden (e.g., decrease tumor size or reduce the number of cancer cells in the body).

In another aspect, a method of treating an angiogenesis-related disease in a subject in need thereof is provided, the method comprising administering a therapeutically effective amount of the antibody, antigen-binding fragment thereof or pharmaceutical composition described herein. For example, the angiogenesis-related disease is a disease selected from neovascular glaucoma, corneal neovascularization, pterygium, retinal vein occlusions, retinal and macular neovascularization from myopia, inflammatory condition, inherited retinal dystrophies, and sickle cell retinopathy, arthritis, synovitis, osteomyelitis, osteophyte formation, multiple sclerosis, vascular malformations, autoimmune diseases, atherosclerosis, transplant arteriopathy, obesity, psoriasis, warts, allergic dermatitis, scar keloids, pyogenic granulomas, blistering disease, Kaposi sarcoma (e.g., in AIDS patients), primary pulmonary hypertension, asthma, nasal polyps, inflammatory bowel disease, periodontal disease, liver cirrhosis, ascites, peritoneal adhesions, endometriosis, uterine bleeding, ovarian cysts, ovarian hyperstimulation, restenosis, and cystic fibrosis.

The foregoing summary is not intended to define every aspect of the invention, and other features and advantages of the present disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Where aspects of the disclosure are described as "methods of treatment," it will be appreciated that uses of the disclosed antibody or antigen-binding fragment thereof for the referenced disease or disorders also is contemplated. For example, the disclosure contemplates use of the antibody or antigen-binding fragment thereof described herein for treating neovascular age-related macular degeneration in a subject in need thereof; treating diabetic retinopathy in a subject in need thereof; or treating retinopathy of prematurity in a subject in need; treating an angiogenesis-related disease in the eye, optionally selected from neovascular glaucoma, corneal neovascularization, pterygium, retinal vein occlusions, retinal and macular neovascularization from myopia, inflammatory condition, inherited retinal dystrophies, and sickle cell retinopathy, in a subject in need thereof. Additional features and variations of the disclosure will be apparent to those skilled in the art from the entirety of this application, and all such features are intended as aspects of the disclosure.

BRIEF DESCRIPTION OF THE FIGURES

FIG. 1A shows the results of endothelial proliferation assays with human umbilical vein endothelial cells (HUVECs) treated with Scg3 (1 µg/mL) or VEGF (50 ng/mL) in 48-well plates (n=4), and FIG. 1B shows the results of endothelial proliferation assays with human retinal microvascular endothelial cells (HRMVECs) treated with Scg3 (1 µg/mL), VEGF (50 ng/mL), or affinity-purified anti-Scg3 polyclonal antibody (pAb) (2 µg/mL) (n=8). The cell number was quantified at 48 h. FIG. 1C to 1E show the results of tube formation assays with HUVECs and the quantification of total tube length per viewing field (FIG. 1C), the number of tubes per viewing field (FIG. 1D) and the number of branching points per viewing field (n=4) (FIG. 1E). FIG. 1F shows spheroid sprouting (average sprout length) of HRMVECs treated with Scg3 (15 ng/mL), VEGF (2.5 ng/mL), or anti-Scg3 pAb (30 µg/mL) (n=8). FIG. 1G shows migration of HRMVECs treated with VEGF and Scg3 (n=3). FIG. 1H shows endothelial permeability in cells treated with phosphate-buffered saline (PBS) (control), VEGF (100 ng/mL) and Scg3 (1 µg/mL) (n=3). FITC-dextran alone with PBS, VEGF, or Scg3 was added to the bottom chamber of a plate with transwell inserts and after 24 hours, media was collected from the top chamber and quantified for leaked FITC. FIG. 1I shows spheroid sprouting (average sprout length) of HUVECs treated with Scg3 (15 ng/mL), VEGF (2.5 ng/mL), or anti-Scg3 pAb (30 μg/mL) (n=8).

FIG. 2A shows the total number of corneal vessels in healthy and diabetic mice treated with PBS, Scg3, hepatoma-derived growth factor-related protein 3 (HRP-3 or Hdgfrp3), and VEGF (left hand bar=healthy; right hand bar=diabetic). FIG. 2B shows the number of vessel branching points. FIG. 2C shows the total angiogenesis score. The studies were blinded, and the n value indicates the number of corneas analyzed. Statistical significance was calculated using a one-way ANOVA test.

FIG. 3A shows anti-Scg3 therapy of DR in Streptozotocin (STZ)-induced diabetic mice treated with anti-Scg3 pAb, mock affinity purified pAb against an irrelevant antigen, control rabbit IgG, anti-Scg3 monoclonal antibody (mAb) Clone 49 (all 0.36 μg/μL/eye), aflibercept (2 μg/μL/eye) or PBS via intravitreal injection. FIG. 3B shows anti-Scg3 mAb inhibited Scg-3-induced HRMVEC proliferation in cells treated with Scg3 (1 μg/mL), VEGF (50 ng/mL), or anti-Scg3 mAb (2 μg/mL) (n=3). FIG. 3C shows anti-Scg3 therapy of DR in Ins2$^{Akita}$ diabetic mice treated with control rabbit IgG (0.36 μg/μL/eye), anti-Scg3 mAb (Clone 49) (0.36 μg/μL/eye), or aflibercept (2 μg/μL/eye) (n=3 to 4). FIG. 3D shows anti-Scg3 therapy of DR in STZ-induced diabetic mice treated with anti-Scg3 mAb Clone 78 (0.36 μg/μL/eye, n=4). Statistical significance was calculated using a one-way ANOVA test. FIG. 3E shows competitive binding to Scg3 for Clone 49, and FIG. 3F shows competitive binding to Scg3 for Clone 78 in the presence of anti-Scg3 mAbs Clone 7, Clone 16, Clone 49, Clone 153, Clone 162, and Clone 190 (n=3). * P<0.05,  P<0.01, * P<0.001, vs. single-chain variable fragment (scFv) alone, t-test.

FIG. 4A shows representative images of OIR in Ins2$^{Akita}$ diabetic mice treated with PBS, control rabbit IgG (0.36 μg/μL/eye), aflibercept (2 μg/μL/eye), anti-Scg3 pAb (0.36 μg/μL/eye) or anti-Scg3 mAb (Clone 49) (0.36 μg/μL/eye) (n=4 to 13). Arrowheads indicate neovascularization (NV) and NV tufts. FIG. 4B shows quantification of NV, FIG. 4C shows quantification of NV tuft number, and FIG. 4D shows quantification of branching points. Statistical significance was calculated using a one-way ANOVA test.

FIG. 5A shows fluorescein angiography images on Day 7, and FIG. 5B shows quantification of CNV fluorescence intensity in FIG. 5A. Mice were sacrificed on Day 8. FIG. 5C shows quantification of CNV 3D volume, FIG. 5D shows quantification of CNV lesion size, and FIG. 5E shows CNV vessel density (i.e., fluorescence intensity). The number of laser spots is indicated at the bottom of the bars, and statistical significance versus control IgG was calculated using a one-way ANOVA test.

FIG. 6A shows anti-Scg3 mAb inhibited Scg3-induced proliferation of HRMVECs. Cells were incubated with Scg3 (1 μg/mL) in the presence or absence of anti-Scg3 Clone 49 mAb (2 μg/mL) for 48 h. Cell number per well was quantified (n=6). FIG. 6B shows anti-Scg3 mAb blocked Scg3-induced activation of Src kinase. HRMVECS were incubated with Scg3 (1 μg/mL) in the presence or absence of anti-Scg3 Clone 49 mAb (2 μg/mL) for 10 min and analyzed by Western blot. FIG. 6C shows quantification of phosphorylated Src (P-Src) signal intensity (n=5).

FIG. 7A shows representative images of fluorescein angiography. Matrigel was injected subretinally on Day 0. Rabbit control IgG (25 μg/kg body weight), mouse control IgG1 (25 μg/kg), aflibercept (250 μg/kg), anti-Scg3 pAb (25 μg/kg) or anti-Scg3 mAb Clone 49 or Clone 78 (25 μg/kg) was subcutaneously injected on Days 0, 2, and 4. Fluorescein angiography was performed on Day 7 to analyze CNV leakage. FIG. 7B shows quantification of CNV leakage in mice treated with Rabbit control IgG, mouse control IgG1, aflibercept, anti-Scg3 pAb or anti-Scg3 mAb Clone 49. The number of mice tested is indicated at the bottom of the bars, and statistical significance was calculated using a one-way ANOVA test. FIG. 7C shows representative images of fluorescein angiography in mice treated with anti-Scg3 mAb Clone 78. FIG. 7D shows quantification of CNV leakage in mice treated with Control IgG and anti-Scg3 mAb Clone 78.

FIGS. 8A to 8C depict regulation of Scg3 and VEGF expression. FIG. 8A shows a Western blot from HRMVECs treated with Scg3 (1 μg/mL) and VEGF (100 ng/mL) indicated that Scg3 does not regulate VEGF expression, or vice versa (n=6). FIG. 8B shows quantification of Scg3 expression (n=5). FIG. 8C shows quantification of VEGF expression (n=3).

FIGS. 9A and 9B depict anti-Scg3 therapy of cancer. FIG. 9A shows comparative ligandomics analysis indicating that Scg3 is a tumor-associated endothelial ligand. FIG. 9B shows that administration of anti-Scg3 mAb intraperitoneally significantly reduced the size of human breast cancer xenografts in mice compared to control mouse IgG1 (n=4).

DETAILED DESCRIPTION

Figure 1A:
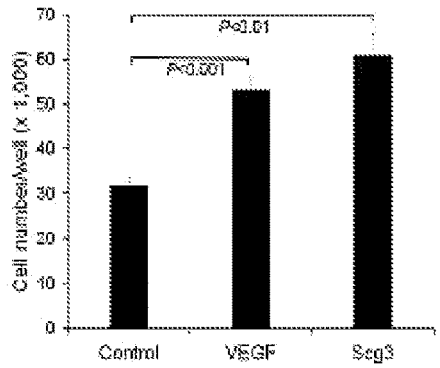
FIGS. 1A to 1I depict in vitro characterizations of Scg3 as an angiogenic factor.

The disclosure provides anti-Scg3 antibodies, and fragments and derivatives thereof, and methods of their use, e.g., in treating DR, nAMD, ROP, and cancer.

Secretogranin III (Scg3 or 1B1075) belongs to the granin family, which regulates the biogenesis of secretory granules (Hosaka and Watanabe. *Endocrine journal.* 2010; 57(4): 275-86; Taupenot et al. *N Engl J Med.* 2003; 348(12):1134-49). Other members of the granin family include chromogranin A (CgA), chromogranin B (CgB) and secretogranin II-VII (Scg2-7) (Helle K B. *Biol Rev Camb Philos Soc.* 2004; 79(4):769-94). CgA can regulate angiogenesis (Helle and Corti. *Cell Mol Life Sci.* 2015; 72(2):339-48). Scg3 is a binding partner of CgA and plays an important role in secretory granule biogenesis and peptide hormone secretion (Hosaka and Watanabe. *Endocrine journal.* 2010; 57(4): 275-86). Scg3 was reported to be secreted from dysfunctional β-cells and therefore may be upregulated in type 1 diabetes (Dowling et al. *Electrophoresis.* 2008; 29(20): 4141-9). Scg3 is released from activated platelets in atherosclerotic lesions (Coppinger et al. *Blood.* 2004; 103(6):2096-104), which are among the vascular complications of diabetes (Rask-Madsen and King. *Cell Metab.* 2013; 17(1): 20-33). Like its other family members, Scg3 is a classical signal peptide can be secreted into the extracellular space (Dowling et al. *Electrophoresis.* 2008; 29(20):4141-9).

Scg3 has not been reported as a cellular ligand or angiogenic factor. Scg3 as a target for anti-angiogenesis therapy is discussed in U.S. patent application Ser. No. 14/708,073, incorporated herein by reference. The present disclosure relates to anti-Scg3 therapy, e.g., anti-Scg3 mAbs, which provide the advantages of unique disease-associated activity, high efficacy, minimal side effects, flexible administration routes and a distinct signaling pathway from VEGF, for the treatment and prevention of DR, nAMD, and cancer.

The following definitions may be useful in aiding the skilled practitioner in understanding the disclosure. Unless otherwise defined herein, scientific and technical terms used in the present disclosure shall have the meanings that are commonly understood by those of ordinary skill in the art. Further, unless otherwise required by context, singular terms shall include pluralities, and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. In practicing the present invention, many conventional techniques in molecular biology, microbiology, cell biology, biochemistry, and immunology are used, which are within the skill of the art. Such techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions, are hereby incorporated by reference as part of the present disclosure.

As used herein, "antibody" or "antibodies" refers to their ordinary meanings in the biochemical and biotechnological arts. Among antibodies within the meaning of the term as it is used herein are those isolated from biological sources, e.g., antibodies produced by hybridoma, antibodies made by recombinant DNA techniques (also referred to at times herein as recombinant antibodies), including those made by processes that involve activating an endogenous gene and those that involve expression of an exogenous expression construct, including antibodies made in cell culture and those made in transgenic plants and animals, and antibodies made by methods involving chemical synthesis, including peptide synthesis and semi-synthesis. Within the scope of the term as it is used herein, except as otherwise explicitly set forth, are monoclonal antibodies, chimeric antibodies, humanized antibodies, and multivalent (e.g., bispecific) antibodies, among others. In one aspect, the antibody is not a polyclonal antibody. The prototypical antibody is a tetrameric glycoprotein comprised of two identical light chain-heavy chain dimers joined together by disulfide bonds. There are two types of vertebrate light chains, kappa and lambda. Each light chain is comprised of a constant region and a variable region. The kappa and lambda light chains are distinguished by their constant region sequences. There are five types of vertebrate heavy chains: alpha, delta, epsilon, gamma, and mu, which define the antibody's isotype as IgM, IgD, IgG, IgA, and IgE, respectively. Each heavy chain is comprised of a variable region and a constant region, which usually comprise three domains. The VH and VL regions can be further subdivided into regions of hypervariability, termed CDRs, interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The heavy and light chains form two regions: the Fab (fragment, antigen binding) region, also referred to as the variable (Fv) region, and the Fc (fragment, crystallizable) region. The variable regions (Fv) of the heavy and light chains contain a binding domain that interacts with an antigen. The constant (Fc) regions of the antibodies may mediate the binding to host tissues or factors, including various cells of the immune system (e.g., effector cells) and the first component (Clq) of the classical complement system. The terms "antibody" and "antibodies" as referred to herein includes whole, full length antibodies (e.g., immunoglobulins having two heavy chains and two light chains). It will be appreciated that the characteristics of antibodies described herein also apply to any fragment or derivative thereof in which the antigen-binding region(s) or single chains thereof are retained.

The term "antigen-binding region" of an antibody refers to the region or portion that confers antigen specificity; antigen-binding fragments of, therefore, include portions of the antibody that retain the ability to specifically bind to an antigen (e.g., an HLA-peptide complex).

The term "fragment" as used herein refers to a polypeptide that has an amino-terminal and/or carboxy-terminal deletion as compared to a corresponding full-length antibody. Examples of antibody fragments encompassed within the term "fragments" include a Fab fragment; a monovalent fragment consisting of the VL, VH, CL and CH1 domains; a F(ab')2 fragment; a bivalent fragment comprising two Fab fragments linked by a disulfide bridge at the hinge region; a Fd fragment consisting of the VH and CH1 domains; a Fv fragment consisting of the VL and VH domains of a single arm of an antibody; a single domain antibody (dAb) (Ward et al. *Nature* 1989; 341:544-546), which consists of a VH domain; an isolated CDR; and a scFv.

The term "derivative" refers to an antibody or antigen-binding fragment thereof that has been chemically modified, e.g., via conjugation to another chemical moiety (such as, for example, polyethylene glycol or albumin, e.g., human serum albumin), phosphorylation, and/or glycosylation.

A "scFv" is a monovalent molecule that can be engineered by joining, using recombinant methods, the two domains of the Fv fragment, VL and VH, by a synthetic linker that enables them to be made as a single protein chain (see e.g., Bird et al. *Science,* 1988; 242:423-426; and Huston et al. *Proc. Natl. Acad. Sci.* 1988; 85:5879-5883). Such single chain antigen-binding peptides are also intended to be encompassed within the term "antibody." These antibody fragments are obtained using conventional techniques known to those of skill in the art, and the fragments are screened for utility in the same manner as are intact antibodies.

The terms "cross-block," "cross-blocked" and "cross-blocking" are used interchangeably herein to mean the ability of an antibody or other antigen-binding protein to interfere with (e.g., inhibit) the binding of other antibodies or antigen-binding proteins to Scg3. Methods of detecting cross-blocking are described below.

The terms "therapeutically effective" or "effective" depends on the condition of a subject and the specific antibody or antigen-binding fragment thereof administered. The terms refer to an amount effective to achieve a desired clinical effect. An effective amount varies with the nature of the condition being treated, the length of time that activity is desired, and the age and the condition of the subject, and ultimately is determined by the health care provider. In various aspects, a therapeutically effective amount is an amount effective to prevent, delay the onset of, or reduce the severity of, a symptom associated with a disease or disorder described herein (e.g., DR, nAMD, ROP, and diseases related to excessive angiogenesis) including angiogenesis (e.g., PDR), apoptosis of endothelial cells and/or pericytes, vascular leakage (e.g., retinal vascular leakage), leukocyte adhesion, acellular capillaries, microaneurisms, retinal vein occlusion, neovascularization (e.g., choroidal and retinal), vision loss, and combinations of any of the foregoing. In another aspect, a therapeutically effective amount is an amount effective to reduce tumor burden, inhibit cell proliferation (e.g., cancer cell proliferation), decrease tumor size, inhibit tumor growth, or a combination of any of the foregoing.

The terms "treating," "treat," "treatment," and the like include preventative (e.g., prophylactic), palliative, remedial, and curative therapies.

The present disclosure provides antibodies and antigen-binding fragments thereof that specifically bind to Scg3, e.g., anti-Scg3 monoclonal antibodies. In one aspect, an antibody or antigen-binding fragment thereof that binds Scg3 and comprises CDR-H1, CDR-H2, CDR-H3, CDR-L1, CDR-L2, and CDR-L3, wherein (a) CDR-H1 comprises an amino acid sequence selected from the group consisting of SEQ ID NOs: 3, 11, 19, and 27; (b) CDR-H2 comprises an amino acid sequence selected from the group consisting of SEQ ID NOs: 4, 12, and 20; (c) CDR-13 comprises an amino acid sequence selected from the group consisting of SEQ ID NOs: 5, 13, 21, and 28; (d) CDR-L1 comprises an amino acid sequence selected from the group consisting of SEQ ID NOs: 6, 14, 22, and 32; (e) CDR-L2 comprises an amino acid sequence selected from the group consisting of SEQ ID NOs: 7, 15, 23, and 29; and (f) CDR-L3 comprises an amino acid sequence selected from the group consisting of SEQ ID NOs: 8, 16, and 24. In another aspect, an antibody or antigen-binding fragment thereof that binds secretogranin III comprises a heavy chain variable domain comprising an amino acid sequence at least 90% identical to SEQ ID NO: 1, 9, 17, 25, 30, 38, or 34, and comprising a light chain variable region comprising an amino acid sequence at least 90% identical to SEQ ID NO: 2, 10, 18, 26, 31, 33, or 35.

Sequence information for the antibodies and antigen-binding fragments described herein are provided in Table 1 (CDR sequences underlined).

TABLE 1

| Ab region | Amino Acid Sequence | SEQ ID NO. |
|---|---|---|
| CLONE 7 Monoclonal Antibody | | |
| Heavy Chain (H) | QVKLEESGPELLKPGASVKISCKTSGYIFSSSWMNWVKQ RPGQGLEWIGRIYPGDGHTNYNGKFKDKATLTADKSSST AYMQLSSLTSVDSAVYFCARLADGYFFVYWGQGTPVTV SA | 1 |
| Light Chain (L) | DIVLTQSPASLAVSLGQRATISCRASKSVSTSGYSYMHW YQQKPGQPPKLLIYLASNLESGVPARFSGSGSGTDFTLNI HPVEEEDAATYYCQHSRELPWTFGGGTKLEIKRA | 2 |
| CDR-H1 | GYIFSSSWMN | 3 |
| CDR-H2 | RIYPGDGHTNYNGKFKD | 4 |
| CDR-H3 | LADGYFFVY | 5 |
| CDR-L1 | RASKSVSTSGYSYMH | 6 |
| CDR-L2 | LASNLES | 7 |
| CDR-L3 | QHSRELPWT | 8 |
| CLONE 49 Monoclonal Antibody | | |
| Heavy Chain (H) | EVKLEESGAELVKPGASVKLSCTASGFNIKDTYMHWVK QRPEQGLEWIGRIDPANGDTKYDPKFQGKATITADTSSN TAYLQLSSLTSEDTAVYYCARNGPGTPWFAYWGQGTLV TVSA | 9 |
| Light Chain (L) | DIQMTQSSSYLSVSLGGRVTITCKASDHINNWLTWYQQK PGNAPRLLISGATSLETGVPSRFSGSGSGKDYTLSITSLQT EDVATYYCQQYWSTPFTFGSGTKLEIKRA | 10 |
| CDR-H1 | GFNIKDTYMH | 11 |
| CDR-H2 | RIDPANGDTKYDPKFQG | 12 |
| CDR-H3 | NGPGTPWFAY | 13 |
| CDR-L1 | KASDHINNWLT | 14 |

TABLE 1-continued

| Ab region | Amino Acid Sequence | SEQ ID NO. |
|---|---|---|
| CDR-L2 | GATSLET | 15 |
| CDR-L3 | QQYWSTPFT | 16 |
| CLONE 78 Monoclonal Antibody | | |
| Heavy Chain (H) | EVQLQQSGPELLKPGASVKISCKTSGYIFSASWMNWVKQRPGQGLEWIGRIYPGDGHTNYNGKIKDKATLTADKSSSTAYMQLSSLTSVDSAVYFCARSADGYFFVDWGQGTLVTVSA | 17 |
| Light Chain (L) | DIVMTQTPVSLPVSLGDQASISCRSSQSIVHSNGNTYLEWYLQKPGQSPKILLIFKVSKRFYGVPDRFSGSGSGTDFTLKISRVEAEDLGVYHCFQGSHVPPTFGGGTKLEIKRA | 18 |
| CDR-H1 | GYIFSASWMN | 19 |
| CDR-H2 | RIYPGDGHTNYNGKIKD | 20 |
| CDR-H3 | SADGYFFVD | 21 |
| CDR-L1 | RSSQSIVHSNGNTYLE | 22 |
| CDR-L2 | KVSKRFY | 23 |
| CDR-L3 | FQGSHVPPT | 24 |
| CLONE 153 Monoclonal Antibody | | |
| Heavy Chain (H) | GRKLQESGPELLKPGASVKISCKTSGYIFSTSWMNWVKQRPGQGLEWIGRIYPGDGHTNYNGKFKDKATLTADKSSSTAYMQLSSLTSVDSAVYFCARSADGYFFVYWGQGTLVTVSA | 25 |
| Light Chain (L) | DIVLTQTPLSLPVSLGDQASISCRSSQSIVHSNGNTYLEWYLQKPGQSPKLLIFKVSKRFSGVPDRFSGSGSGTDFTLKISRVEAEDLGVYHCFQGSHVPPTFGGGTKLEIKRA | 26 |
| CDR-H1 | GYIFSTSWMN | 27 |
| CDR-H2 | RIYPGDGHTNYNGKFKD | 4 |
| CDR-H3 | SADGYFFVY | 28 |
| CDR-L1 | RSSQSIVHSNGNTYLE | 22 |
| CDR-L2 | KVSKRFS | 29 |
| CDR-L3 | FQGSHVPPT | 24 |
| CLONE 162 Monoclonal Antibody | | |
| Heavy Chain (H) | PGKAEESGPEMLKPGASVKISCKTSGYIFSTSWMNWVKQRPGQGLEWIGRIYPGDGHTNYNGKFKDKATLTADKSSSTAYMQLSSLTSADSAVYFCARSADGYFFVYWGQGTLVTVSA | 30 |
| Light Chain (L) | DIVLTQTPLSLPVSLGDQASISCRSSQNIIHSNGNTYLEWYLQKPGQSPKLLIFKVSKRFSGVPDRFSGSGSGTDFTLKISRVEAEDLGVYHCFQGSHVPPTFGGGTKLEIKRA | 31 |
| CDR-H1 | GYIFSTSWMN | 27 |
| CDR-H2 | RIYPGDGHTNYNGKFKD | 4 |
| CDR-H3 | SADGYFFVY | 28 |
| CDR-L1 | RSSQNIIHSNGNTYLE | 32 |
| CDR-L2 | KVSKRFS | 29 |
| CDR-L3 | FQGSHVPPT | 24 |

TABLE 1-continued

| Ab region | Amino Acid Sequence | SEQ ID NO. |
|---|---|---|
| CLONE 16 Monoclonal Antibody | | |
| Heavy Chain (H) | EVKLEQSGPELLKPGASVKISCKTSGYIFSSSWMNWVKQ RPGQGLEWIGRIYPGDGHTNYNGKFKDKATLTADKSSST AYMQLSSLTSVDSAVYFCARSADGYFFVYWGQGTPVTV SA | 38 |
| Light Chain (L) | DIVLTQTPLSLPVSLGDQASISCRSSQSIVHSNGNTYLEW YLQKPGQSPKLLIFKVSKRFSGVPDRFSGSGLGTDFTLKI SRVGAEDLGIYYCFQGSHVPPTFGGGTKLEIKRA | 33 |
| CDR-H1 | GYIFSSSWMN | 3 |
| CDR-H2 | RIYPGDGHTNYNGKFKD | 4 |
| CDR-H3 | SADGYFFVY | 28 |
| CDR-L1 | RSSQSIVHSNGNTYLE | 22 |
| CDR-L2 | KVSKRFS | 29 |
| CDR-L3 | FQGSHVPPT | 24 |
| CLONE 190 Monoclonal Antibody | | |
| Heavy Chain (H) | EVKLEESGPELLKPGASVKISCKTSGYIFSSSWMNWVKQ RPGQGLEWIGRIYPGDGHTNYNGKFKDKATLTADKSSST AYMQLSSLTSVDSAVYFCARSADGYFFVYWGQGTPVTV SA | 34 |
| Light Chain (L) | DIVMTQSPLSLPVSLGDQASISCRSSQSIVHSNGNTYLEW YLQKPGQSPKLLIFKVSKRFSGVPDRFSGSGSGTDFTLKI SRVGAEDLGIYYCFQGSHVPPTFGGGTKLEIKRA | 35 |
| CDR-H1 | GYIFSSSWMN | 3 |
| CDR-H2 | RIYPGDGHTNYNGKFKD | 4 |
| CDR-H3 | SADGYFFVY | 28 |
| CDR-L1 | RSSQSIVHSNGNTYLE | 22 |
| CDR-L2 | KVSKRFS | 29 |
| CDR-L3 | FQGSHVPPT | 24 |

In one example, the antibody or antigen-binding fragment thereof comprises CDR-H1, CDR-H2, CDR-H3, CDR-L1, CDR-L2, and CDR-L3, wherein (a) CDR-H1 comprises SEQ ID NO: 3; (b) CDR-H2 comprises SEQ ID NO: 4; (c) CDR-H3 comprises SEQ ID NO: 5; (d) CDR-L1 comprises SEQ ID NO: 6; (e) CDR-L2 comprises SEQ ID NO: 7; and (f) CDR-L3 comprises SEQ ID NO: 8. Optionally, the antibody or antigen-binding fragment thereof comprises a heavy chain variable region comprising an amino acid sequence at least 90% identical to SEQ ID NO: 1 and a light chain variable region comprising an amino acid sequence at least 90% identical to SEQ ID NO: 2.

In another example, the antibody or antigen-binding fragment thereof comprises CDR-H1, CDR-H2, CDR-H3, CDR-L1, CDR-L2, and CDR-L3, wherein (a) CDR-H1 comprises SEQ ID NO: 11; (b) CDR-H2 comprises SEQ ID NO: 12; (c) CDR-H3 comprises SEQ ID NO: 13; (d) CDR-L1 comprises SEQ ID NO: 14; (e) CDR-L2 comprises SEQ ID NO: 15; and (f) CDR-L3 comprises SEQ ID NO: 16. Optionally, the antibody or antigen-binding fragment thereof comprises a heavy chain variable region comprising an amino acid sequence at least 90% identical to SEQ ID NO: 9 and a light chain variable region comprising an amino acid sequence at least 90% identical to SEQ ID NO: 10.

In still another example, the antibody or antigen-binding fragment thereof comprises CDR-H1, CDR-H2, CDR-H3, CDR-L1, CDR-L2, and CDR-L3, wherein (a) CDR-H1 comprises SEQ ID NO: 19; (b) CDR-H2 comprises SEQ ID NO: 20; (c) CDR-H3 comprises SEQ ID NO: 21; (d) CDR-L1 comprises SEQ ID NO: 22; (e) CDR-L2 comprises SEQ ID NO: 23; and (f) CDR-L3 comprises SEQ ID NO: 24. Optionally, the antibody or antigen-binding fragment thereof comprises a heavy chain variable region comprising an amino acid sequence at least 90% identical to SEQ ID NO: 17 and a light chain variable region comprising an amino acid sequence at least 90% identical to SEQ ID NO: 18.

In one example, the antibody or antigen-binding fragment thereof comprises CDR-H1, CDR-H2, CDR-H3, CDR-L1, CDR-L2, and CDR-L3, wherein (a) CDR-H1 comprises SEQ ID NO: 27; (b) CDR-H2 comprises SEQ ID NO: 4; (c) CDR-H3 comprises SEQ ID NO: 28; (d) CDR-L1 comprises SEQ ID NO: 22; (e) CDR-L2 comprises SEQ ID NO: 29; and (f) CDR-L3 comprises SEQ ID NO: 24. Optionally, the antibody or antigen-binding fragment thereof comprises a heavy chain variable region comprising an amino acid sequence at least 90% identical to SEQ ID NO: 25 and a light chain variable region comprising an amino acid sequence at least 90% identical to SEQ ID NO: 26.

In another example, the antibody or antigen-binding fragment thereof comprises CDR-H1, CDR-H2, CDR-H3, CDR-L1, CDR-L2, and CDR-L3, wherein (a) CDR-H1 comprises SEQ ID NO: 27; (b) CDR-H2 comprises SEQ ID NO: 4; (c) CDR-H3 comprises SEQ ID NO: 28; (d) CDR-L1 comprises SEQ ID NO: 32; (e) CDR-L2 comprises SEQ ID NO: 29; and (f) CDR-L3 comprises SEQ ID NO: 24. Optionally, the antibody or antigen-binding fragment thereof comprises a heavy chain variable region comprising an amino acid sequence at least 90% identical to SEQ ID NO: 30 and a light chain variable region comprising an amino acid sequence at least 90% identical to SEQ ID NO: 31.

In still another example, the antibody or antigen-binding fragment thereof comprises CDR-H1, CDR-H2, CDR-H3, CDR-L1, CDR-L2, and CDR-L3, wherein (a) CDR-H1 comprises SEQ ID NO: 3; (b) CDR-H2 comprises SEQ ID NO: 4; (c) CDR-H3 comprises SEQ ID NO: 28; (d) CDR-L1 comprises SEQ ID NO: 22; (e) CDR-L2 comprises SEQ ID NO: 29; and (f) CDR-L3 comprises SEQ ID NO: 24. Optionally, the antibody or antigen-binding fragment thereof comprises a heavy chain variable region comprising an amino acid sequence at least 90% identical to SEQ ID NO: 38 or 34 and a light chain variable region comprising an amino acid sequence at least 90% identical to SEQ ID NO: 33 or 35.

For any of the antibodies or antigen-binding fragments thereof disclosed herein comprising a heavy chain variable domain comprising an amino acid sequence at least 90% identical to SEQ ID NO: 1, 9, 17, 25, 30, 38, or 34, and comprising a light chain variable region comprising an amino acid sequence at least 90% identical to SEQ ID NO: 2, 10, 18, 26, 31, 33, or 35, the heavy chain variable domain and/or light chain variable region is at least 90%, at least 91%, at least 92%, at least 93%, at least 94%, at least 95%, at least 96%, at least 97%, at least 98%, at least 99%, or 100% identical to one of the foregoing SEQ ID NOs.

In one aspect, the antigen-binding fragment is a Fab fragment, a F(ab')2 fragment, or a scFv.

In another aspect, the disclosure provides an antibody or antigen-binding fragment thereof that cross-blocks a reference antibody from binding to secretogranin III, wherein the reference antibody is selected from the group consisting of an antibody comprising CDRs of SEQ ID NOs: 3-8; an antibody comprising CDRs of SEQ ID NOs: 11-16; an antibody comprising CDRs of SEQ ID NOs: 19-24; an antibody comprising CDRs of SEQ ID NOs: 27, 4, 28, 22, 29, and 24; an antibody comprising CDRs of SEQ ID NOs: 27, 4, 28, 32, 29, and 24; and an antibody comprising CDRs of SEQ ID NOs: 3, 4, 28, 22, 29, and 24. For example, the reference antibody is selected from the group consisting of an antibody comprising a heavy chain variable region comprising SEQ ID NO: 1 and a light chain variable region comprising SEQ ID NO: 2; an antibody comprising a heavy chain variable region comprising SEQ ID NO: 9 and a light chain variable region comprising SEQ ID NO: 10; an antibody comprising a heavy chain variable region comprising SEQ ID NO: 17 and a light chain variable region comprising SEQ ID NO: 18; an antibody comprising a heavy chain variable region comprising SEQ ID NO: 25 and a light chain variable region comprising SEQ ID NO: 26; an antibody comprising a heavy chain variable region comprising SEQ ID NO: 30 and a light chain variable region comprising SEQ ID NO: 31; an antibody comprising a heavy chain variable region comprising SEQ ID NO: 38 and a light chain variable region comprising SEQ ID NO: 33; and an antibody comprising a heavy chain variable region comprising SEQ ID NO: 34 and a light chain variable region comprising SEQ ID NO: 35.

The antibody or antigen-binding fragment thereof is produced using any suitable method, e.g., isolated from an immunized animal, recombinantly or synthetically generated, or genetically-engineered. For example, monoclonal antibodies that bind to specific antigens may be obtained by methods known to those skilled in the art (see, for example, Kohler et al. *Nature* 256:495, 1975; Coligan et al. (eds.), *Current Protocols in Immunology*, 1:2.5.12.6.7 (John Wiley & Sons 1991); U.S. Pat. Nos. RE 32,011, 4,902,614, 4,543, 439, and 4,411,993; *Monoclonal Antibodies, Hybridomas: A New Dimension in Biological Analyses*, Plenum Press, Kennett, McKearn, and Bechtol (eds.) (1980); and *Antibodies: A Laboratory Manual*, Harlow and Lane (eds.), Cold Spring Harbor Laboratory Press (1988); Picksley et al. "Production of monoclonal antibodies against proteins expressed in *E. coli*," in *DNA Cloning 2: Expression Systems, 2nd Edition*, Glover et al. (eds.), page 93 (Oxford University Press 1995)). Monoclonal antibodies can be obtained by injecting an animal, for example, a rat, hamster, a rabbit, or preferably a mouse, including for example a transgenic or a knock-out, as known in the art, with an immunogen comprising human Scg3, or a fragment thereof, according to methods known in the art and described herein. The presence of specific antibody production may be monitored after the initial injection and/or after a booster injection by obtaining a serum sample and detecting the presence of an antibody that binds to human Scg3 or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines. The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human Scg3, using any one of a variety of immunoassays known in the art and described herein. The hybridomas are cloned (e.g., by limited dilution cloning or by soft agar plaque isolation) and positive clones that produce an antibody specific to Scg3 are selected and cultured. The monoclonal antibodies from the hybridoma cultures may be isolated from the supernatants of hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody, and a TGF-beta binding protein, or fragment or variant thereof.

Fragments, derivatives, or analogs of antibodies can also be readily prepared using techniques well-known in the art. Antigen-binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; *Porter, Biochem. J.* 73:119, 1959; Edelman et al., in *Methods in Enzymology* 1:422 (Academic Press 1967); and by Andrews, S. M. and Titus, J. A. in *Current Protocols in Immunology* (Coligan J. E. et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody or fragment thereof also can be genetically engineered. For example, in various aspects, the antibody or antibody fragment comprises, e.g., a variable region domain generated by recombinant DNA engineering techniques. In this regard, an antibody variable region is optionally modified by insertions, deletions, or changes in the amino acid sequence of the antibody to produce an antibody of interest. Polynucleotides encoding CDRs of interest are prepared, for example, by using polymerase chain reaction or gene synthesis to synthesize variable regions using mRNA of antibody producing cells as a template (see, for example, Courtenay Luck, "Genetic Manipulation of Monoclonal Antibodies," in *Monoclonal Antibodies: Production, Engineering and Clinical Application*, Ritter et al. (eds.), page 166 (Cambridge University Press 1995); Ward et al., "Genetic Manipulation and Expression of Antibodies," in *Monoclonal Antibodies: Principles and Applications*, Birch et al., (eds.), page 137 (Wiley Liss, Inc. 1995); and Larrick et al., *Methods: A Companion to Methods in Enzymology*, 2: 106-110, 1991). Current antibody manipulation techniques allow construction of engineered variable region domains containing at least one CDR and, optionally, one or more framework amino acids from a first antibody and the remainder of the variable region domain from a second antibody. Such techniques are used, e.g., to humanize an antibody or to improve its affinity for a binding target. Humanized antibodies are antibodies in which CDRs of heavy and light variable chains of non-human immunoglobulin are transferred into a human variable domain. Constant regions need not be present, but if they are, they optionally are substantially identical to human immunoglobulin constant regions, i.e., at least about 85-90%, about 95% or more identical, in various embodiments. Hence, in some instances, all parts of a humanized immunoglobulin, except possibly the CDRs, are substantially identical to corresponding parts of natural human immunoglobulin sequences. For example, in one aspect, humanized antibodies are human immunoglobulins (host antibody) in which hypervariable region residues of the host antibody are replaced by hypervariable region residues from a non-human species (donor antibody) such as mouse, rat, rabbit, or a non-human primate having the desired specificity, affinity, and capacity.

One form of an antigen-binding fragment of an antibody is a peptide comprising one or more complementarity determining regions (CDRs) of the antibody. CDRs (also termed "minimal recognition units", or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Thus, in one embodiment, the antigen-binding fragment thereof comprises at least one CDR as described herein. The antigen-binding fragment thereof may comprise at least two, three, four, five or six CDR's as described herein. The antibody or antigen-binding fragment thereof further may comprise at least one variable region domain of an antibody described herein. The variable region domain may be of any size or amino acid composition and will generally comprise at least one CDR sequence responsible for binding to human Scg3, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or VL domain, which is capable of independently binding Sgc3 with an affinity at least equal to $1\times10^{-7}$ M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as Fv). If desired, the chains may be covalently coupled either directly, for example via a disulfide bond between the two variable domains, or through a linker, for example a peptide linker, to form a single chain Fv (scFv).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

In certain embodiments, the antibody or antigen-binding fragment thereof may be chemically bonded with polymers, lipids, or other moieties. For example, the antibody or antigen-binding fragment thereof may comprise one or more water soluble polymer attachments, including, but not limited to, polyethylene glycol, polyoxyethylene glycol, or polypropylene glycol. See, e.g., U.S. Pat. Nos. 4,640,835; 4,496,689; 4,301,144; 4,670,417; 4,791,192; and 4,179,337. In certain embodiments, an antibody or antigen-binding fragment derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426; which is hereby incorporated by reference for any purpose.

The antibody or fragment thereof preferentially binds to Scg3, meaning that the antibody or fragment thereof binds Scg3 with greater affinity than it binds to an unrelated control protein. More preferably, the antibody or fragment thereof specifically recognizes and binds Scg3 or a portion thereof. "Specific binding" means that the antibody or fragment thereof binds to Scg3 with an affinity that is at least 5, 10, 15, 20, 25, 50, 100, 250, 500, 1000, or 10,000 times greater than the affinity for an unrelated control protein. In some variations, the antibody or fragment thereof binds Scg3 substantially exclusively, i.e., is able to distinguish Scg3 from other known polypeptides (e.g., other granins) by virtue of measurable differences in binding affinity. An antibody or fragment thereof may have a binding affinity for Scg3 of less than or equal to $1\times10^{-7}$ M, less than or equal to $1\times10^{-8}$ M, less than or equal to $1\times10^{-9}$ M, less than or equal to $1\times10^{-10}$ M, less than or equal to $1\times10^{-11}$ M, or less than or equal to $1\times10^{-12}$ M. Affinity may be determined by an affinity ELISA assay. In certain embodiments, affinity may be determined by a BIAcore (GE Healthcare Bio-Sciences, Pittsburgh, Pa.) or Octet (Pall ForteBio, Menlo Park, Calif.) assay. In certain embodiments, affinity may be determined by a kinetic method. In certain embodiments, affinity may be determined by an equilibrium/solution method. Such methods are described in further detail herein or known in the art.

In various aspects, the antibody or antigen-binding fragments thereof modulates Scg3 function in the cell-based assay described herein and/or the in vivo assay described herein and/or cross-blocks the binding of one of the antibodies described in this application and/or is cross-blocked from binding Scg3 by one of the antibodies described in this application. Accordingly such antibody or antigen-binding fragments thereof can be identified using the assays described herein.

It will be appreciated that an antibody or antigen-binding fragment of the present disclosure may have at least one amino acid substitution relative to the amino acid sequences provided herein, providing that the binding agent retains binding specificity. Therefore, modifications to the antibodies or antigen-binding fragments thereof are encompassed within the scope of the invention. These may include amino acid substitutions, which may be conservative or non-conservative, that do not destroy the Scg3-binding capability of an antibody or antigen-binding fragment thereof. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position. Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing an amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

An antibody or antigen-binding fragment thereof is within the scope of the disclosure if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDRs of Table 1 above; and/or to a CDR of an anti-Scg3 antibody that cross-blocks the binding of at least one of the antibodies in Table 1 to Scg3; and/or is cross-blocked from binding to Scg3 by at least one of antibodies in Table 1; and/or to a CDR of an anti-Scg3 antibody, wherein the an anti-Scg3 antibody can block the effect of Scg3 in a cell-based assay. An antibody or antigen-binding fragment thereof is also within the scope of the invention if it has an amino acid sequence that is at least 85%, 86%, 87%, 88%, 89%, 90%, 91%, 92%, 93%, 94%, 95%, 96%, 97%, 98% or 99% identical to a variable region of at least one of the antibodies in Table 1 and cross-blocks the binding of at least one of the antibodies in Table 1 to Scg3, and/or is cross-blocked from binding to Scg3 by at least one of antibodies the antibodies in Table 1; and/or can block the effects of Scg3 in a cell-based assay.

In one aspect, the disclosure provides a nucleic acid encoding an antibody or antigen-binding fragment thereof described herein. The disclosure also provides an expression vector comprising said nucleic acid. A nucleic acid coding for each CDR sequence may be determined on the basis of the amino acid sequence of the CDR and synthesized together with any desired antibody variable region framework and constant region polynucleotide sequences using oligonucleotide synthesis techniques, site-directed mutagenesis and polymerase chain reaction (PCR) techniques as appropriate. Coding for variable region frameworks and constant regions is widely available to those skilled in the art from genetic sequences databases such as GENBANK.

In one aspect, the disclosure provides for a host cell transfected with an expression vector or nucleic acid encoding an antibody or antigen-binding fragment described herein. In certain embodiments, expression of an antibody fragment may be preferred in a prokaryotic host cell, such as *Escherichia coli* (see, e.g., Pluckthun et al., *Methods Enzymol.* 1989; 178:497-515). In certain other embodiments, expression of the antibody or a fragment thereof may be preferred in a eukaryotic host cell, including yeast (e.g., *Saccharomyces cerevisiae, Schizosaccharomyces pombe,* and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells. Particular methods for producing antibodies in this way are generally well-known and routinely used. For example, basic molecular biology procedures are described by Maniatis et al. (Molecular Cloning, *A Laboratory Manual*, 2nd ed., Cold Spring Harbor Laboratory, New York, 1989; see also Maniatis et al., 3rd ed., Cold Spring Harbor Laboratory, New York, (2001)). DNA sequencing can be performed (e.g., as described in Sanger et al., *PNAS* 1977; 74:5463) and site-directed mutagenesis can be carried out according to methods known in the art (Kramer et al., *Nucleic Acids Res.* 1984; 12:9441; Kunkel *Proc. Natl. Acad. Sci. USA* 1985; 82:488-92; Kunkel et al., *Methods in Enzymol.* 1987; 154:367-82). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York). It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 1995; 705:129-134).

Optionally, the affinity of antibodies or antigen-binding fragments thereof is improved by any of a number of affinity maturation protocols including maintaining the CDRs (Yang et al., *J. Mol. Biol.*, 1995; 254:392-403), chain shuffling (Marks et al., *Bio/Technology* 1992; 10:779-783), use of mutation strains of *E. coli.* (Low et al., *J. Mol. Biol.*, 250, 350-368, 1996), DNA shuffling (Patten et al., *Curr. Opin. Biotechnol.*, 8, 724-733, 1997), and phage display (Thompson et al., *J. Mol. Biol.*, 256, 7-88, 1996). Additional methods of affinity maturation are discussed by Vaughan et al., *Nature Biotechnology* 1998; 16, 535-539).

The affinity of an antibody or fragment thereof, as well as the extent to which an antibody or fragment thereof inhibits binding, can be determined by one of ordinary skill in the art using conventional techniques, for example those described by Scatchard et al., *Ann. N.Y. Acad. Sci.* 51:660-672 (1949) or by surface plasmon resonance (SPR; BIAcore) or by an Octet assay. For SPR, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al. *Cancer Res.* 53:2560-65 (1993)). For Octet affinity quantification, antigen is labeled with biotin and binds to streptavidin on the probe. Antibody binding to antigen is quantified in a similar manner to BIAcore by detecting changes in the intensity of the reflected light. Antibody binding affinity can be quantified in a similar manner (Estep et al., *MAbs.* 5:270-278 (2013)).

An antibody according to the present invention may belong to any immunoglobin class, for example IgG, IgE, IgM, IgD, or IgA. In various embodiments, the antibody is an IgG, such as an IgG2 or IgG4. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in, for example, U.S. Patent Publication No. 2004/0146888 A1.

The extent to which an antibody or other binding agent is able to interfere with the binding of another to Scg3, and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay is the Octet assay. Another suitable quantitative cross-blocking assay uses an ELISA-based approach to measure competition between antibodies or other binding agents in terms of their binding to Scg3. Cross-blocking (i.e., competition) assays are described in the art, such as International Patent Publication No. WO 2006/119107.

In one aspect, the disclosure provides a pharmaceutical composition comprising an anti-Scg3 antibody or antigen-binding fragment thereof described herein along with a pharmaceutically or physiologically acceptable carrier, excipient, or diluent. A composition comprising an anti-Scg3 antibody may be in any suitable dosage form including, but not limited to, tablets, capsules, implants, depots, liquids, patches, lozenges, creams, gels, ointments, lotions, sprays, ear drops, and eye drops. The particular carrier employed is limited only by chemico-physical considerations, such as solubility and lack of reactivity with the antibody or co-therapy, and by the route of administration. Physiologically acceptable carriers are well-known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., *Pharmaceutics and Pharmacy Practice*, J. B. Lippincott Co., Philadelphia. Pa., Banker and Chalmers. eds., pages 238-250 (1982), and *ASHP Handbook on Injectable Drugs*, Toissel, 4th ed., pages 622-630 (1986)). A pharmaceutical composition comprising the anti-Scg3 antibody is, in one aspect, placed within containers, along with packaging material that provides instructions regarding the use of such pharmaceutical compositions, e.g., in a kit. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition. The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

Suitable methods of administering such pharmaceutical compositions are well-known in the art. Although more than one route can be used to administer an agent (such as the antibody or antigen-binding fragment described herein), a particular route can provide a more immediate and more effective reaction than another route. Depending on the circumstances, a pharmaceutical composition comprising the anti-Scg3 antibody or antigen-binding fragment thereof is applied or instilled into body cavities, absorbed through the skin or mucous membranes, ingested, inhaled, administering to the eye, and/or introduced into circulation. For example, in certain circumstances, it will be desirable to deliver a pharmaceutical composition comprising the agent orally, through injection or infusion by intravenous, subcutaneous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the composition (or antibody or antigen-binding fragment thereof) is administered regionally via intraarterial or intravenous administration feeding the region of interest. Alternatively, the composition is administered locally via implantation of a membrane, sponge, or another appropriate material on to which the desired molecule has been absorbed or encapsulated, for example, as described in Mylonas et al., *Curr Eye Res. Epub* Sep. 9, 2016, and Birch et al., *Am J Ophthalmol.* 2013; 156(2):283-292. Where an implantation device is used, the device is, one aspect, implanted into any suitable tissue or organ, and delivery of the desired molecule is, for example, via diffusion, timed-release bolus, or continuous administration. In other aspects, the agent is administered directly to exposed tissue during tumor resection or other surgical procedures. In one aspect, the pharmaceutical composition is administered locally to the eye, e.g., ophthalmically, intraocularly, conjunctivally, intracorneally, intravitreally, and/or retrobulbarly. Therapeutic delivery approaches are well known to the skilled artisan, some of which are further described, for example, in U.S. Pat. No. 5,399,363.

A particular administration regimen for a particular subject will depend, in part, upon the antibody or antigen-binding fragment used, the amount of antibody or antigen-binding fragment administered, the route of administration, and the cause and extent of any side effects. The amount of antibody or antibody fragment administered to a subject (e.g., a mammal, such as a human) in accordance with the invention should be sufficient to effect the desired response over a reasonable time frame. In various aspects, the method comprises administering, e.g., from about 0.1 µg/kg to up to about 400 mg/kg or more (e.g., 0.1 µg/kg to up to about 100 mg/kg or more). For example, the dosage ranges from about 0.1 µg/kg up to about 10 mg/kg; or about 5 gg/kg up to about 100 mg/kg; or about 10 µg/kg up to about 100 mg/kg; or about 1 mg/kg up to about 50 mg/kg; or about 2 mg/kg up to about 30 mg/kg; or about 3 mg/kg up to about 25 mg/kg; or about 3 mg/kg up to about 25 mg/kg; or about 5 mg/kg up to about 10 mg/kg; or about 10 mg/kg up to about 20 mg/kg; or about 10 mg/kg up to about 30 mg/kg; or about 50 mg/kg up to about 300 mg/kg; or about 100 mg/kg up to about 250 mg/kg; or about 100 mg/kg up to about 200 mg/kg. In various aspects, the method comprises administering, e.g., from about 0.05 mg to about 10 mg, to an eye of a human subject, for example, about 0.1 mg to about 0.5 mg, about 0.05 mg to about 1 mg, about 0.2 mg to about 2 mg, about 0.5 mg to about 2.5 mg, about 2 mg to about 4 mg, or about 1 mg to about 5 mg. Some conditions or disease states require prolonged treatment, which may or may not entail administering doses of anti-Scg3 therapy over multiple administrations (e.g., every day, 3 times a week, once a week, once every 2 weeks, or once every month for a treatment period of 3 days, 7 days, 2 weeks, 3 weeks, 1 month, 3 months, 6 months, 9 months, 12 months, 15 months, 18 months, 21 months, 2 years, or more).

In one aspect, the disclosure provides a method of treating neovascular age-related macular degeneration in a subject in need thereof comprising administering a therapeutically effective amount of an antibody or antigen-binding fragment thereof or pharmaceutical composition comprising the same described herein. In one aspect, the antibody, antigen-binding fragment thereof, or pharmaceutical composition is administered in an amount effective to inhibit choroidal neovascularization.

In another aspect, the disclosure provides a method of treating diabetic retinopathy (including diabetic macular edema (DME) and/or proliferative diabetic retinopathy (PDR)) or retinopathy of prematurity in a subject in need thereof comprising administering a therapeutically effective amount of an antibody or antigen-binding fragment thereof or pharmaceutical composition comprising the same described herein. In one aspect, the antibody, antigen-binding fragment thereof, or pharmaceutical composition is administered in an amount effective to inhibit retinal vascular leakage and/or retinal neovascularization.

In one aspect, the antibody or antigen-binding fragment thereof or pharmaceutical composition comprising the same is administered in an amount effective to inhibit choroidal neovascularization and/or retinal neovascularization. Choroidal neovascularization and/or retinal neovascularization is inhibited, for example, by at least 10%, at least 20%, at least 30%, at least 40%, at least 50%, at least 60%, at least 70%, at least 80%, at least 90%, or at least 100%, compared to before administration of the antibody, antigen-binding fragment thereof, or pharmaceutical composition. Methods of measuring choroidal and/or retinal neovascularization are known in the art, including, for example, imaging techniques including angiography (e.g., using fluroscein or indocyanine green), and optical coherence tomography (OCT).

In another aspect, the antibody or antigen-binding fragment thereof or pharmaceutical composition comprising the same is administered in an amount effective to decrease retinal vascular leakage compared to before treatment. Retinal vascular leakage is inhibited, for example, by at least 10%, at least 20%, at least 30%, at least 40%, at least 50%, at least 60%, at least 70%, at least 80%, at least 90%, or at least 100%, compared to before administration of the antibody, antigen-binding fragment thereof, or pharmaceutical composition. Methods of measuring retinal vascular leakage are known in the art, including, for example, retinal permeability assays (e.g., using Evans blue dye or a fluorescent label), and imaging techniques including angiography (e.g., using fluroscein or indocyanine green), and OCT.

In another aspect, the antibody or antigen-binding fragment thereof or pharmaceutical composition comprising the same is administered in an amount effective to treat cancer. The method comprises contacting cancer cells with an amount of an antibody or antigen-binding fragment thereof or pharmaceutical composition comprising the same described herein effective to inhibit proliferation of the cancer cells or modulate tumor growth. In some embodiments, the cancer cells are in a subject, and the contacting comprises administering a therapeutically effective amount of the antibody or antigen-binding fragment thereof or pharmaceutical composition to the subject. It will be understood that the antibodies and antigen binding fragments thereof of the disclosure can be used in methods of inhibiting cancer cell proliferation in vitro and in vivo (e.g., in a method of treating cancer in a subject). Examples of cancers and tumors include, but are not limited to, bladder cancer, breast cancer, colorectal cancer, endometrial cancer, eye cancer (e.g., retinoblastoma, uveal melanoma, and intraocular lymphoma), kidney cancer, leukemia, lung cancer, lymphoma, pancreatic cancer, prostate cancer, skin cancer, brain cancer, thyroid cancer, liver cancer, oral cancer, oropharyngeal cancer, esophageal cancer, and stomach cancer.

"Inhibiting" cancer cell proliferation does not require a 100% prevention of proliferation. Any reduction in the rate of proliferation is contemplated. Similarly, "modulating" tumor growth refers to reducing the size of the tumor, slowing tumor growth, or inhibiting an increase in the size of an existing tumor. Complete abolition of a tumor is not required; any decrease in tumor size or slowing of tumor growth constitutes a beneficial biological effect in a subject. Tumor mass, volume, and/or length can be assessed using methods known in the art such as calipers, ultrasound imaging, computed tomography (CT) imaging, magnetic resonance imaging (MRI), optical imaging (e.g., bioluminescence and/or fluorescence imaging), digital subtraction angiography (DSA), positron emission tomography (PET) imaging and/or other imaging analysis. Tumor cell proliferation can also be analyzed using cellular assays that measure, e.g., DNA synthesis, metabolic activity, antigens associated with cell proliferation, and/or ATP. In various embodiments, the method of the present disclosure reduces the size of a tumor at least about 5% (e.g., at least about 10%, at least about 15%, at least about 25%, at least about 30%, at least about 40%, at least about 50%, at least about 60%, at least about 70%, or at least about 80%). In this regard, cancer cell proliferation is inhibited by, e.g., at least about 5%, at least about 10% or at least about 20% compared to levels of proliferation observed in the absence of the inventive method (e.g., in a biologically-matched control subject or specimen that is not exposed to an antibody or antigen binding fragment of the disclosure). The effect is detected by, for example, a reduction in tumor size, a decrease or maintenance of the levels of cancer markers, or reduction or maintenance of a cancer cell population. In some embodiments, proliferation is reduced by at least about 30%, at least about 40%, at least about 50%, or at least about 60%, by at least about 70%, at least about 80%, at least about 90%, or more (about 100%), compared to proliferation in the absence of the antibody or antigen binding fragment thereof of the disclosure.

In another aspect, the antibody or antigen-binding fragment thereof or pharmaceutical composition comprising the same is administered in an amount effective to treat a disease related to excessive angiogenesis. Examples of angiogenesis-related diseases include, but are not limited to, diseases in the eye including neovascular glaucoma, corneal neovascularization, pterygium, retinal vein occlusions, retinal and macular neovascularization from myopia, inflammatory condition, inherited retinal dystrophies, and sickle cell retinopathy, as well as non-ocular diseases including arthritis, synovitis, osteomyelitis, osteophyte formation, multiple sclerosis, vascular malformations, autoimmune diseases, atherosclerosis, transplant arteriopathy, obesity, psoriasis, warts, allergic dermatitis, scar keloids, pyogenic granulomas, blistering disease, Kaposi sarcoma (e.g., in AIDS patients), primary pulmonary hypertension, asthma, nasal polyps, inflammatory bowel disease, periodontal disease, liver cirrhosis, ascites, peritoneal adhesions, endometriosis, uterine bleeding, ovarian cysts, ovarian hyperstimulation, restenosis, and cystic fibrosis (see, e.g., Carmeliet, *Nature Medicine* 2003; 9(6):654-660; and Houtman, *FASEB Breakthroughs in Bioscience* 2010; p. 1-17).

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). In various aspects, the disclosure provides use of the antibody or antigen-binding fragment thereof in the preparation of a medicament for the treatment of ocular disorders, including diabetic retinopathy and choroidal neovascularization and other eye-related ailments described herein, as well the treatment of cancer as described herein. The disclosure further provides use of the antibody or antigen-binding fragment thereof in the treatment of ocular disorders, including diabetic retinopathy and choroidal neovascularization and other eye-related ailments described herein, as well use in the treatment of cancer as described herein. Also provided is the antibody or antigen-binding fragment thereof described herein for use in the treatment of ocular disorders, including diabetic retinopathy and choroidal neovascularization and other eye-related ailments described herein, as well as use in the treatment of cancer as described herein. In jurisdictions that do not forbid the patenting of methods that are practiced on the human body, the "administering" of compositions includes both methods practiced on the human body and also the foregoing activities.

The following examples are provided by way of illustration and are not intended to be limiting.

EXAMPLES

Example 1

Anti-Scg3 Therapy for Diabetic Retinopathy

Materials and Methods

Antibodies. Recombinant HRP-3 was prepared as described (LeBlanc et al. *PLoS One.* 2015; 10(5):e0127904). Anti-Scg3 mAb (Clone 49 and Clone 78, mouse IgG1) was raised against human Scg3 (Sino Biological) and purified from serum-free hybridoma-conditioned medium using protein G columns. Anti-c-Myc mAb was purified from the conditioned medium of 9E10 hybridoma and used as mouse control IgG1. Control rabbit IgG was purified from rabbit serum.

Diabetic mice. C57BL/6 mice (6 weeks old, male; Jackson Laboratory) were induced for type 1 diabetes with streptozocin (STZ; Sigma) or mock citrate buffer, as described (Zhong et al. *Diabetes.* 2012; 61(2):492-504). Briefly, mice were starved for 4 h and then received STZ (40 µg/g body weight) or sodium citrate buffer (137 mM, pH 4.5) via intraperitoneal injection for 5 consecutive days. STZ was dissolved in the citrate buffer (7.5 mg/ml) immediately before the injection. Mice were monitored for blood glucose biweekly and considered diabetic when blood glucose was ≥350 mg/dL, usually starting at 2 weeks post STZ treatment. Mice were aged for 4 months post STZ to develop DR.

Heterozygous Ins2$^{Akita}$ mice (Jackson Laboratory), which developed hyperglycemia by 4-6 weeks of age, were monitored for blood glucose. The diabetic phenotype and associated complications are more severe and progressive in the males than in females. Ins2$^{Akita}$ males developed retinal vascular leakage at 6 months of age and therefore were chosen for anti-Scg3 therapy in this study.

Clonal phages. Clonal phages were constructed as described (Caberoy et al. *J Biomol Screen.* 2009; 14(6):653-61). Briefly, the coding sequences of green fluorescent protein (GFP) with no stop codon was amplified by PCR, digested and cloned into T7Bio3C phage vector (Caberoy et al. *J Mol Recognit.* 2010; 23(1):74-83) at NotI and XhoI sites to generate GFP-Phage. The coding sequence for wild-type human VEGF$_{1-110}$ (hVEGF) with artificial codons was designed, commercially synthesized (GenScript) and cloned into T7Bio3C at NotI and XhoI sites to generate hVEGF-Phage. Both clonal phages were verified by sequencing.

OPD library purification. Open reading frame phage display (OPD) libraries derived from mouse adult eyes and E18 embryos were described previously (Caberoy et al. *J Biomol Screen.* 2009; 14(6):653-61; Caberoy et al. *J Mol Recognit.* 2010; 23(1):74-83). Next generation DNA sequencing (NGS) analysis of unselected libraries indicated that the combined libraries consist of at least 9,500 different proteins. The OPD libraries and control clonal phages were amplified and purified according to Novagen T7Select System Manual (Millipore) with modifications. Briefly, BLT5615 bacteria were cultured in LB medium to OD$_{600}$ at 0.5 and induced with isopropyl β-D-1-thiogalactopyranoside (IPTG; 1 mM) at 37° C. for 30 min with shaking. The libraries or the control clonal phages (~4×10$^9$ plaque form unit (pfu)) were added to IPTG-induced BLT5615 (200 ml) and incubated with shaking at 37° C. until bacterial lysis. After additional 15-min incubation with DNase 1(40 µg), the two libraries were pooled in equal phage titer to improve library representation. hVEGF-Phage and GFP-Phage were mixed in equal titer and diluted into the pooled libraries at 1:1,000 ratio. After adding and dissolving NaCl (10 g), the combined library lysate was centrifuged at 13,200×g for 10 min at 4° C. Polyethylene glycol 8000 (PEG-8000, 40 g) was added and dissolved in the supernatant, which was incubated at 4° C. overnight and centrifuged under the same condition. The phage pellet was resuspended in Tris-NaCl buffer (1 M NaCl, 10 mM Tris-HCl, pH 8.0, 1 mM EDTA) and centrifuged. The supernatant was laid on a discontinuous CsCl gradient (20.8%, 31.25%, 41.7% and 62.5%, w/v) and centrifuged in Beckman SW41 rotor at 35,000 rpm for 60 min at 23° C. A phage band right above 41.7% CsCl was collected, dialyzed against PBS and titrated by phage plaque assay.

In vivo binding selection. Diabetic and control C57BL/6 mice (23 weeks old or 4 months after STZ) were anesthetized by intraperitoneal injection of ketamine (90 µg/g) and xylazine (8 µg/g). The purified library was intravenously injected into anesthetized mice (3 mice/group/round, 1×10$^{12}$ pfu/mouse) and circulated for 20 min. Unbound phages were removed by intracardial perfusion with PBS. Retinas were isolated and homogenized in PBS containing 1% Triton X-100 to release endothelium-bound phages. Aliquots of the lysates were used to quantify phage titer by plaque assay, as described. The remaining phages in the lysates were amplified in IPTG-induced BLT5615 bacteria and repurified as above. Purified phages were used as input for the next round of in vivo selection. After 3 rounds of selection, the cDNA inserts of enriched phage clones were amplified by PCR with primer 5'-GCGGTTCAGGCTCGCGGCCG-3' (SEQ ID NO: 36) and 5'-CCGCTCCCACTACCCTCGAG-3' (SEQ ID NO:37). PCR products between 400-1,500 bp were purified from agarose gel and identified by NGS.

Comparative ligandomic data analysis. NGS data were aligned against NCBI CCDS database to identify enriched ligands. The copy numbers of cDNA inserts identified by NGS represent the relative binding activities of their cognate ligands to retinal endothelium and were quantitatively compared by Chi-square test to identify DR-associated ligands. CCDS ID of NGS data were batch-converted to Uniprot accession numbers and analyzed by PANTHER and DAVID. Identified ligands were categorized based on gene ontology (GO) terms "Cellular Component" and "Biological Process."

Cell proliferation assay. HRMVECs (Cell Systems) or HUVECs (Lonza) at 4-8 passages were cultured with Scg3, VEGF165 or PBS control at the indicated concentrations in 96- or 48-well plates as described (LeBlanc et al. *PLoS One.* 2015; 10(5):e0127904). When needed, affinity-purified anti-Scg3 pAb or mAb was washed three times with PBS in Amicon centrifugal filter units (10 kDa), concentrated and added to cells. Fresh medium, growth factors and antibody were added every 24 h. Cells in each well were collected by trypsin digestion at 48 h, resuspended in PBS with 1 mM trypan blue and quantified.

Tube formation assay. The assay was carried out as described (LeBlanc et al. *PLoS One*. 2015; 10(5):e0127904). Briefly, Matrigel was diluted 1:4 (vol/vol) in EBM-2 medium, plated in 96-well plates (50 µl/well) and allowed to solidify at 37° C. for 30 min. HUVECs were starved in serum-free 293 SFM II medium (Life Technologies) overnight, harvested and plated on Matrigel (15,000 cells/well). Cells were incubated with Scg3, VEGF or PBS in 293 SFM II medium at 37° C. for 4 h. Bright field images were taken. Total tube length, number of tubes and number of branching points per viewing field were quantified using ImageJ software (NIH).

Wound healing assay. Cell migration was analyzed by in vitro wound healing assay as described (LeBlanc et al. *PLoS One*. 2015; 10(5):e0127904). Briefly, HMRVECs were cultured in 12-well plates until ~90-100% confluence and starved for 3 h in 293 SFM II medium supplemented with 0.2% FBS. A sterile 200-µl tip was used to create a defined and clear scratch approximate 1 mm in width in each well. After rinsing, cells were cultured in fresh 293 SFM II medium containing 0.2% FBS in the presence of Scg3 or VEGF. Cell migration was monitored at 0 and 20 h by phase-contrast microscopy. The percentage of the denuded area covered by migrated cells within the original scratch was quantified using ImageJ.

In vitro endothelial permeability assay. The assay was performed as described (Martins-Green et al. *Methods Enzymol*. 2008; 443(137-53). HUVECs were plated in transwell inserts in 24-well plates and cultured to confluence. FITC-dextran (3-5 kDa) (1 mg/ml) was added to the bottom chamber along with Scg3, VEGF or PBS. After 24 h, FITC concentration in the upper chamber was quantified using a fluorescence plate reader and calculated against a standard curve.

Spheroid sprouting. The assay was performed with HRMVECs as described (LeBlanc et al. *PLoS One*. 2015; 10(5):e0127904). Briefly, methocel solution was prepared by dissolving methylcellulose in EBM-2 medium at 1.2% (w/v) and centrifuged at 5,000×g for 2 h at 4° C. to clear debris. Cells at 80% confluence were harvested, counted, resuspended in EBM-2 medium containing 20% methocel and 10% fetal bovine serum (FBS), seeded at 750 cells/well in non-adhesive 96-well round-bottomed plates and cultured for 24 h. Spheroids were harvested, resuspended in EBM-2 medium containing fibrinogen (2.5 mg/ml) and aprotinin (0.05 mg/ml), and seeded in 24-well plates (~50 spheroids/ml/well). Clotting was induced by adding thrombin (12 units/ml) to each well. The spheroid-embedded fibrin gel was allowed to clot for 5 min at room temperature and then 20 min at 37° C. The fibrin gel was incubated with Scg3, VEGF or PBS with or without anti-Scg3 mAb in the basal medium containing 0.05 mg/ml aprotinin for 48 h. Photographs were taken using a phase contrast microscope, and average sprout lengths were quantified using ImageJ.

Protein pulldown. Scg3 (5 µg/ml) was incubated with aflibercept, VEGFR-Fc or VEGFR2-Fc (5 µg/ml) in PBS solution containing 0.5% Triton X-100 and BSA (1 mg/ml) for 1 h at 4° C. Protein G beads (20 µl) were added and incubated at 4° C. for 30 min with end-over-end rotation. The beads were washed three times with PBS by centrifugation, eluted with low pH buffer (100 mM glycine, pH 2.7) and analyzed by Western blot using anti-Scg3 pAb.

ERK activation. ERK1/2 activation was detected as described (LeBlanc et al. *PLoS One*. 2015; 10(5):e0127904). HUVECs were preincubated in 293 SFM II medium for 15 min×3 times at 37° C. to reduce the effect of other growth factors. Cells were incubated with Scg3, VEGF or PBS in EBM-2 medium for 10 or 30 min in 37° C., lysed and analyzed by Western blot using antibody against phosphorylated ERK1/2 (pEKR1/2), ERK1/2 or β-actin.

Akt activation. Akt activation was performed in a similar manner as EKR activation. HUVECs were preincubated with 293 SFM II medium for 15 min×4 times. Cells were incubated with Scg3, VEGF or PBS for 10 min in 37° C., lysed and analyzed by Western blot using antibody against phosphorylated Akt T308 (pAkt), total Akt or β-actin.

Immunohistochemistry. Immunohistochemical analysis of mouse retina was performed using affinity-purified anti-Scg3 pAb as described (Guo et al. *Molecular biology of the cell*. 2015; 26(12):2311-20). Briefly, anesthetized mice (C57BL/6, 8 weeks old) were intracardially perfused with 10% formalin. Eyes were isolated and fixed overnight at 4° C. After removal of the cornea and lens, eye cups were incubated with sucrose gradient solutions (10% and 20% for 3 h each; 30% for overnight) at 4° C., followed by 3 rounds of freeze-thaw and OCT (optimal cutting temperature compound) embedding. Frozen tissue sections in 7-µm thickness were incubated with anti-Scg3 pAb, followed by Alexa Fluor 488-labeled goat anti-rabbit IgG antibody. The nuclei were visualized with DAPI. Signals were analyzed by confocal microscopy.

Scg3 expression in the retina and vitreous fluid. The vitreous fluid (2 µl/eye) was collected from 4-month-diabetic and age-matched control mice. Their retinas were isolated and homogenized in SDS-PAGE loading buffer. Samples were analyzed by Western blot using anti-Scg3 pAb or anti-β-actin antibody.

Corneal angiogenesis assay. The assay was carried out as described (LeBlanc et al. *PLoS One*. 2015; 10(5):e0127904). Briefly, sterilized Whatman filter paper (Grade 3) was cut into pieces (0.125 mm$^2$/piece) and soaked in the solution of Scg3 (0.25 µg/µl), VEGF (0.1 g/µl), HRP-3 (1 µg/µl) or PBS for 2 h at 4° C. Soaked papers were implanted into corneal pockets of anesthetized C57BL/6 mice (8 weeks old; 1 paper/cornea; 2 pockets/mouse, one eye always for PBS). After 6 days, corneal angiogenesis was evaluated using a slit-lamp microscope and photographed. The number of new sprouting vessels into the cornea, their branching points and semiquantitative score were quantified and normalized against PBS in fellow eyes. Mice were then euthanized by $CO_2$ and immediately perfused intracardially with fluorescent DiI dye. Flat-mounted corneas were analyzed by confocal microscopy to detect DiI-labeled blood vessels.

Evans blue assay. Retinal vascular leakage was quantified by Evans blue (EB) assay as described (Scheppke et al. *J Clin Invest*. 2008; 118(6):2337-46). Briefly, affinity-purified anti-Scg3 pAb, affinity-purified pAb against an irrelevant antigen (Plekha1) (mock control), rabbit control IgG, anti-Scg3 mAb and mouse control IgG1 were washed three times in Amicon centrifugal filter units (10 kDa) with PBS and concentrated. Anti-Scg3 mAb, mock affinity-purified pAb, rabbit control IgG, anti-Scg3 mAb, mouse control IgG1 (0.36 µg/µl/eye) or aflibercept (2 µg/1 µl/eye) was intravitreally injected into one eye of diabetic mice with PBS for contralateral eyes. EB (0.15 mg/g body weight) was intravenously injected 1.5 h post intravitreal injection. Anesthetized mice were intracardially perfused with pre-warmed (37° C.) sodium citrate solution (100 mM, pH 4.5) 2.5 h post EB injection. Retinas were isolated and incubated with formamide (50 µl/retina) at 70° C. overnight to extract EB. The solutions were centrifuged at 180,000×g at 4° C. for 1 h. EB in the supernatant was quantified at 620 nm and 740 nm (background) and compared to a standard curve. Blood samples were collected from EB-injected mice before intracardial perfusion, directly centrifuged at 3,550×g for 15 min at 25° C., diluted and quantified at the same wavelengths. EB leakage was calculated with the following formula: [leaked EB concentration (mg/ml)/retinal weight (mg)]/[blood EB concentration (mg/ml)×circulation time (h)]. Data are normalized to PBS in contralateral eyes and expressed as percentage of reduction in leakage.

Oxygen-induced retinopathy (OIR). OIR was performed as described (LeBlanc et al. *Mol Vis.* 2016; 22L374-86; Connor et al. *Nat Protoc.* 2009; 4(11):1565-73). Briefly, mice (C57BL/6) at postnatal day 7 (P7) were exposed to 75% oxygen in a regulated chamber. At P12, anti-Scg3 pAb, control IgG, anti-Scg3 mAb (0.36 µg/1 µl/eye), aflibercept (2 µg/1 µl/eye) or PBS was intravitreally injected into anesthetized mice, which were returned to room air after the injection. At P17, mice were euthanized by $CO_2$ inhalation. Isolated retinas were stained with Alexa Fluor 488-isolectin B4, flat-mounted and analyzed by confocal microscopy. Neovascularization was quantified as described (Connor et al. *Nat Protoc.* 2009; 4(11):1565-73). Additionally, the number of neovascular tufts was quantified throughout the entire retina. The number of branching points within a defined area was quantified in the same region of each retina. All data are normalized against non-injection eyes.

Statistics. Data are expressed as mean±SEM. Intergroup differences were analyzed by one-way ANOVA test or Student's t-test. NGS datasets were compared by Chi-square test.

Results

Quantitative ligandomic profiling. Cellular ligands, such as angiogenic factors, are traditionally identified by technically-challenging, low-throughput approaches. It is even more daunting to delineate pathogenic ligands with therapeutic potential. To tackle the challenge, open reading frame phage display (OPD) was developed for the unbiased identification of cellular ligands in the absence of receptor information. OPD was further combined with next generation sequencing (NGS) as the first paradigm of ligandomics to globally map cell-wide endothelial ligands. In this example, comparative ligandomics was applied to diabetic and control mice to systematically identify DR-associated endothelial ligands and investigate their pathological role and therapeutic potential.

To establish DR in mice, type 1 diabetes was induced with streptozotocin (STZ), which destroys β islet cells, and hyperglycemic mice were aged for 4 months to develop DR. As expected, a 3.4-fold increase in retinal vascular leakage in diabetic mice was observed. For ligandomic analysis, OPD libraries were intravenously injected into diabetic and mock-treated control mice for three rounds of in vivo binding selection to enrich for retinal endothelial ligands (Fieger et al. *J Biol Chem.* 2003; 278(30):27390-8). All the cDNA inserts of enriched clones were analyzed by NGS. A total of 489,126 and 473,965 valid sequence reads were identified and aligned to 1,548 (diabetic retina) and 844 (healthy retina) proteins in the NCBI CCDS database. The identified ligands are involved in diverse cellular processes, ~11.5% of which are related to angiogenesis, apoptosis, cell migration and adhesion.

It was predicted that the copy numbers of cDNA inserts identified by NGS correlate with the endothelial binding activity of their cognate ligands. To confirm this correlation, two clonal phages expressing either human VEGF (hVEGF-Phage, positive control) or green fluorescent protein (GFP-Phage, negative control) were constructed. HVEGF-Phage displays wild-type human VEGF protein, but with artificially altered codons for maximal silent mutations and can be distinguished from endogenous VEGF by NGS. Equal titers of hVEGF-Phage and GFP-Phage with non-mouse codons were diluted into the mouse OPD libraries (1:1,000) before the in vivo selection and identified simultaneously within enriched library clones by NGS. The depletion of GFP-Phage and relative enrichment of hVEGF-Phage in NSG (GFP-Phage vs. VEGF-Phage) after three rounds of selection confirmed that the copy numbers reflected their differential binding activities in vivo. Furthermore, the results established GFP-Phage as a baseline for non-specific binding. It was found that 417/844 and 817/1,548 isolated ligands specifically bound above this baseline to healthy and diabetic retina, respectively.

Identification of Scg3 as a DR-high ligand by comparative ligandomics. The global binding activity patterns for the entire ligandome profiles of diabetic and healthy retinas were relatively similar. However, more detailed comparison revealed subtle differences for individual ligands. Scg3 was detected with 1,731 copies in diabetic retina, but no copies in healthy retina, implying that its receptor(s) may be upregulated on diabetic endothelium. In contrast, the endothelial binding activity of hepatoma-derived growth factor-related protein 3 (Hdgfrp3, HRP-3) to diabetic retina was reduced by 227-fold, implicating that its receptor(s) may be downregulated in diabetes. VEGF binding activity was reduced only by 5.9-fold, suggesting that retinal endothelial expression of VEGF receptors was minimally altered in 4-month-diabetic mice.

As a proof-of-concept for comparative ligandomics, quantitative comparison of the entire ligandome profiles for diabetic vs. control retina by Chi-square ($\chi^2$) test was performed. There were 1,114 DR-associated endothelial ligands (p<0.05) identified from a total of 1,772 non-redundant ligands, which were characterized as "DR-high" and "DR-low" ligands based on their increased or decreased binding to diabetic retinal endothelium. However, a plot of the Chi-square value vs. the binding activity ratio for diabetes:control uncovered many ligands with minimal, but statistically significant, changes in binding activity between the two conditions. To improve the reliability of identifying disease-associated ligands, DR-high or DR-low ligands were further defined with the following more stringent, arbitrary criteria: p<0.001; diabetes:control binding activity ratio ≥10 or ≤0.1; copy number in DR or control ≥30. Using these criteria, 353 DR-high and 105 DR-low ligands were obtained (Table 2). Scg3 and HRP-3 were identified as DR-high and DR-low ligands, respectively. Scg2 was also discovered with increased binding to diabetic retinal vessels (Table 3), but was not qualified as a DR-high ligand due to its relatively low binding activity. The changes in global binding activity patterns using an activity plot for all identified ligands was analyzed. The results indicated that endothelial binding activities of the entire ligandome were markedly altered in diabetic mice (Pearson correlation coefficient r=0.498 for 1,772 ligands).

TABLE 2

DR-associated endothelial ligands
identified by comparative ligandomics

| CCDS_ID | Protein | Binding activity DR | Control | Activity ratio |
|---|---|---|---|---|
| \multicolumn{5}{c}{DR-high ligands with increased binding to} | | | | |
| CCDS23347 | Scg3* | 1,731 | 0 | 1,732 |
| CCDS18810 | C1qb* | 837 | 0 | 838 |
| CCDS15031 | Fn1* | 419 | 0 | 420 |
| CCDS35631 | Col4a3* | 409 | 2 | 137 |
| CCDS28285 | APP* | 206 | 1 | 104 |
| CCDS22638 | Cdh1* | 132 | 0 | 133 |
| DR-low ligands with decreased binding to diabetic ECs | | | | |
| CCDS40011 | HRP-3* | 48 | 11,140 | 0.0044 |
| CCDS17457 | HDGF* | 0 | 83 | 0.0119 |
| Internal positive and negative controls | | | | |
| | VEGF-Phage | 408 | 2,420 | 0.1689 |
| | GFP-Phage | 10 | 10 | 1.0 |
| | Total identified sequences | 489,126 | 473,965 | |
| | Total identified ligands | 1,548 | 844 | |
| | Diabetes-related ligands* | 353↑ | 105↓ | |

*P < 0.001, DR vs. control, $\chi^2$ test.
Activity ratio = (DR + 1)/(Control + 1).

TABLE 3

Known or putative endothelial ligands identified by comparative ligandomics

| CCDS_ID | Protein | Binding activity Control | DR | Activity Ratio | Commens & references |
|---|---|---|---|---|---|
| CCDS23347 | Scg3 | 0 | 1731 | 1732.0 | Scg3 is verified as a DR-associated angiogenic factor in this study. |
| CCDS18810 | C1qb | 0 | 837 | 838.0 | C1qb is the β subunit of C1q, which is a known EC ligand (13). |
| CCDS26200 | Jag2 | 0 | 92 | 93.0 | Jag2 is a ligand for Notch1, which id expressed on ECs (14). |
| CCDS20005 | Ptn | 0 | 38 | 39.0 | Ptn is a known angiogenic factor involved in the pathogenesis of PDR (15). |
| CCDS15089 | Seg2 | 0 | 16 | 17.0 | Seg2 is a prohormone of secretoneurin, which is an angiogenic factor (16). |
| CCDS15806 | Notch1 | 0 | 16 | 17.0 | Notch1 is a ligand for Jagged1, which is expressed on ECs (14). |
| CCDS19483 | Sparcl1 | 1,003 | 5,336 | 5.3157 | Sparc modulates cell cycle progress in bovine aortic ECs (17). |
| CCDS19983 | Podxl | 3,877 | 9,349 | 2.4110 | Podxl2 is an L-selectin ligand that is expressed on ECs (18). |
| CCDS16777 | Chgb | 3,531 | 3,910 | 1.1073 | Chromogranin B (Chgb), a member of the granin family, has an undefined role on EC regulation. |
| CCDS51013 | Notch2 | 2,114 | 2,264 | 1.0709 | Notch2 is a ligand for Jagged1, which is expressed on ECs (14). |
| CCDS28578 | Tulp1 | 55,252 | 49,334 | 0.8929 | Tulp1 is a ligand for TAM receptor tyrosine kinase family, similar to Gas6 (see Gas6 below) (19, 20). |
| CCDS40232 | Gas6 | 8,876 | 7,139 | 0.8043 | Gas6 is a ligand for TAM receptor of Tyro3, Axl and Mer receptor tyrosine kinases to regulate ECs (19) |
| CCDS20912 | Apoc | 90 | 61 | 0.6813 | Apolipoprotein E is a potent inhibitor of EC proloiferation (21). |
| CCDS17457 | Hdgf | 83 | 48 | 0.5833 | HDGF is an angiogenic factor (11, 22). |
| CCDS28390 | Plg | 35 | 11 | 0.3333 | Plasminogen binds to EC surface actin to regulate fibrinolysis (23). |
| CCDS16766 | Prnp | 220 | 47 | 0.2172 | Prion protein promotes angiogenesis (24). |
| CCDS24864 | Ntn1 | 11 | 0 | 0.0833 | Netrin-1 inhibits EC apoptosis (25). |
| CCDS17149 | Gnas | 71 | 1 | 0.0278 | Gnas inhibits endothelial proliferation (26). |
| CCDS18100 | Tpm2 | 12,226 | 164 | 0.0136 | Tmp2 is highly homologous to tropomyosin, which extrinisically inhibits angiogensis (27). |
| CCDS40011 | Hdgfrp3 | 11,140 | 48 | 0.0044 | Hdgfrp3 of HRP-3 is an angiogenic factor (1). |
| CCDS16498 | Rcn1 | 23,107 | 71 | 0.0031 | Rcn1 binds to EC surface (28). |
| CCDS14820 | Sulf1 | 338 | 0 | 0.0030 | Sulfatase 1 remodels 6-O-sulfatation on cell surface and inhibits VEGF signaling and angiogensis (29). |

Incluion criteria: binding activity >10 (i.e., the activity of GFP-Phage) in diabetic or control retina. References in the Table are listed in Supplemental References.

3898-910). C1qb is the β subunit of C1q complement factor that interacts with at least two endothelial receptors, cC1qR and gC1qR/p33, to produce proinflammatory cytokines (Vogel et al. *Journal of Cellular Biochemistry*. 1994; 54(3):299-308). C1q is present in significant quantities at the site of atherosclerotic lesions (Peerschke et al. *Mol Immunol*. 2004; 41(8):759-66), which are one of the most common diabetic vascular complications. Hepatoma-derived growth factor (HDGF) is a known mitogenic endothelial ligand (Oliver et al. *J Clin Invest*. 1998; 102(6):1208-19). HRP-3 is in the same protein family as HDGF (Izumoto et al. *Biochem Biophys Res Commun*. 1997; 238(1):26-32) and was independently verified as a DR-low angiogenic factor in this example, implicating that HDGF may be a DR-low ligand as well. Finally, receptor upregulation on diabetic retinal endothelium for adhesion molecules, such as fibronectin 1 (Fn1), collagen type IVα3 (Col4a3) and cadherin 1 (Cdh1), may contribute to leukocyte adhesion in DR (Rask-Madsen et al. *Cell Metab*. 2013; 17(1):20-33; Forbes et al. *Physiol Rev*. 2013; 93(1):137-88).

Figure 1B:
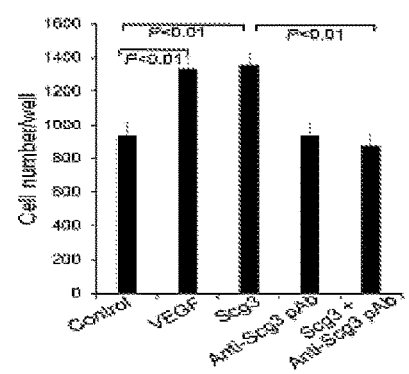
Figure 1C:
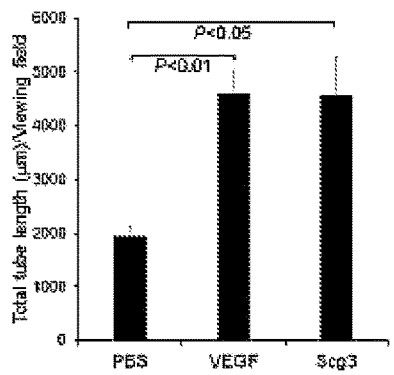
Figure 1D:
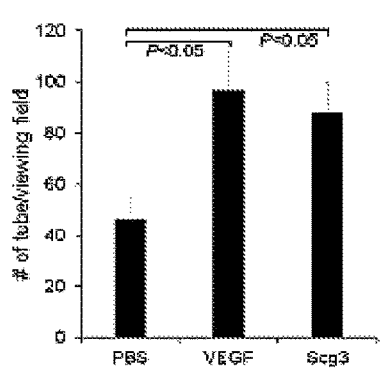
Figure 1E:
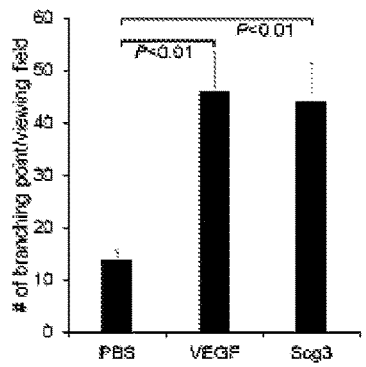
Figure 1F:
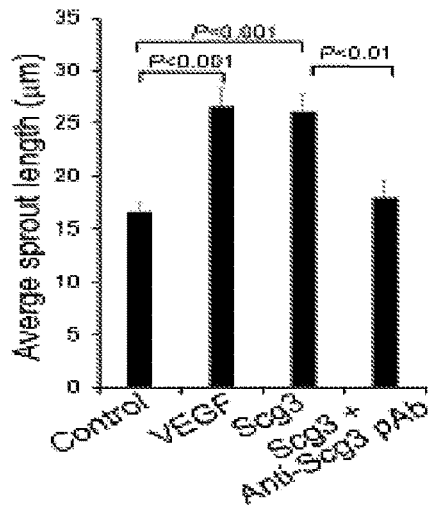
Figure 1G:
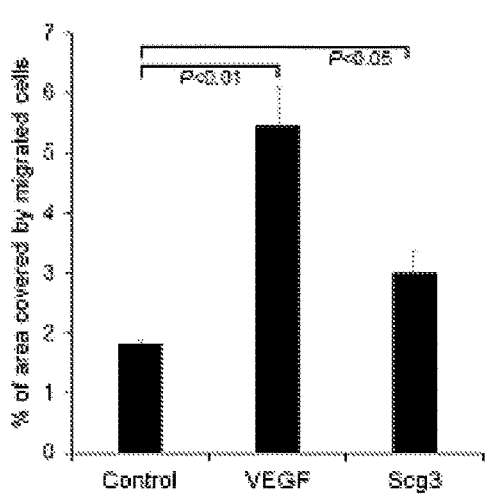
Figure 1H:
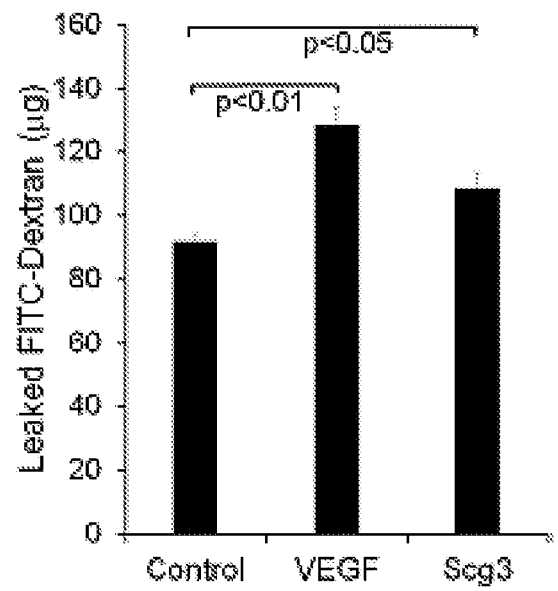

Independent verification of Scg3 as a novel angiogenic factor. To demonstrate the validity of comparative ligandomics, DR-high Scg3 and DR-low HRP-3 were chosen for independent verification of their distinct disease association patterns. These two orphan ligands were selected because of their high-fold changes in binding activity to diabetic retinal endothelium. Additionally, HRP-3 was recently identified as an angiogenic factor in healthy retina by ligandomics (LeBlanc et al. *PLoS One*. 2015; 10(5):e0127904). To determine if Scg3 was also an angiogenic factor, several functional analyses in vitro were performed. Scg3 significantly promoted the proliferation of human umbilical vein endothelial cells (HUVECs) and human retinal microvascular endothe- The validity of comparative ligandomics was supported by the identification of several known and putative diabetes-associated endothelial ligands (Tables 2 and 3). Amyloid β derived from amyloid precursor protein (APP) is a known endothelial ligand and binds to RAGE (receptor for advanced glycation end products), which is upregulated on diabetic endothelium (Caberoy et al. *EMBO J*. 2010; 29(23):

lial cells (HRMVECs) (FIGS. 1A and 1B). Additional analyses showed that Scg3 stimulated tube formation of ECs. The quantification of the tube length, number of branching points and number of the tubes in microscopic analyses confirmed that Scg3 induced the tube formation (FIG. 1C-E). Furthermore, the results revealed that Scg3 significantly promoted spheroid sprouting of HRMVECs (FIG. 1F). The wound healing assay indicated that Scg3 facilitated the migration of HRMVECs (FIG. 1G), and the in vitro permeability assay showed that Scg3 induced endothelial permeability (FIG. 1H). In all these assays, VEGF served as a positive control and significantly stimulated endothelial proliferation, tube formation, migration and permeability.

Scg3 expression in the retina and vitreous fluid of diabetic and control mice were characterized. Immunohistochemistry revealed that Scg3 was expressed in retinal ganglion cells, inner and outer plexiform layers, photoreceptor inner segments and retinal pigment epithelial (RPE) cells. Few Scg3 signals were detected in inner and outer nuclear layers and photoreceptor outer segments. This expression pattern was consistent with its role in secretory granules to regulate neurotransmitter storage and transport. The results further revealed that Scg3 was expressed at a similar level in the homogenates of diabetic and control retina. Scg3 secretion was verified by its presence in the cell-free vitreous fluid of mouse eye by Western blot. Interestingly, Scg3 was significantly upregulated in the vitreous fluid of 4-month-diabetic mice compared to healthy mice, implicating that Scg3 secretion may be a regulated process, similar to the regulated secretion of CTLA-4 (Valk et al. *Trends Immunol.* 2008; 29(6):272-9).

Figure 2A:
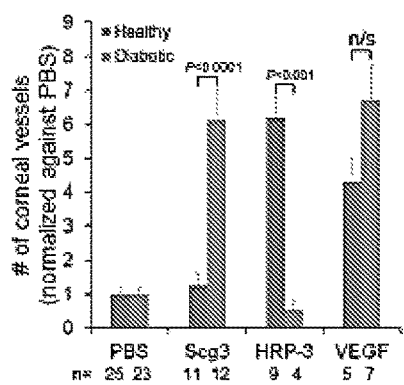
FIGS. 2A to 2C depict quantification of corneal angiogenesis in diabetic and healthy animals.
Figure 2B:
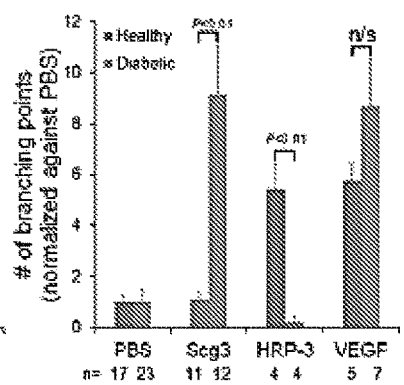
Figure 2C:
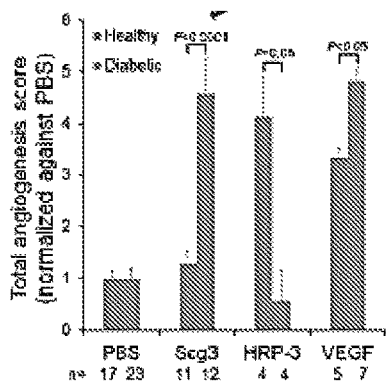

Validation of disease-high and disease-low angiogenic factors. To verify DR-high Scg3 and DR-low HRP-3 as disease-related angiogenic factors, a corneal pocket assay was performed in diabetic and control mice. Scg3 preferentially induced angiogenesis in diabetic mice relative to healthy mice. In contrast, HRP-3 selectively stimulated angiogenesis in healthy, but not diabetic mice. As expected, a control assay with VEGF promoted angiogenesis in both healthy and diabetic mice. These findings were observed not only by slit-lamp examination, but also verified by the staining of corneal vessels with lipophilic fluorescent DiI dye. The quantification of corneal vessels, branching points and a comprehensive score corroborated the opposite angiogenic patterns of Scg3 and HRP-3 (FIG. 2A-2C). The quantifications also verified VEGF had similar activity in both healthy and diabetic mice, except that the comprehensive score indicated more angiogenic activity for VEGF in diabetic mice than in control mice (FIG. 2C). The data indicated that Scg3 and HRP-3 are bona fide diabetes-high and diabetes-low angiogenic factors, respectively, which in turn supported the validity of quantitative and comparative ligandomics.

Different receptor signaling pathways of Scg3 and VEGF. The distinct patterns of corneal angiogenic activity in diabetic and control mice suggested that Scg3 and VEGF may have different receptors and signaling pathways. Indeed, Scg3 failed to interact with aflibercept, an engineered chimeric receptor consisting of the second binding domain of VEGF receptor 1 (VEGFR1) and the third domain of VEGFR2 fused to human IgG Fc. This finding was independently verified by a protein pulldown assay using VEGFR1-Fc and VEGFR2-Fc. Although both Scg3 and VEGF activated ERK1/2, only VEGF, and not Scg3, stimulated the phosphorylation of Akt. These data indicated that Scg3 and VEGF with distinct receptors may partially converge their intracellular signaling to differentially regulate angiogenesis.

Figure 3A:
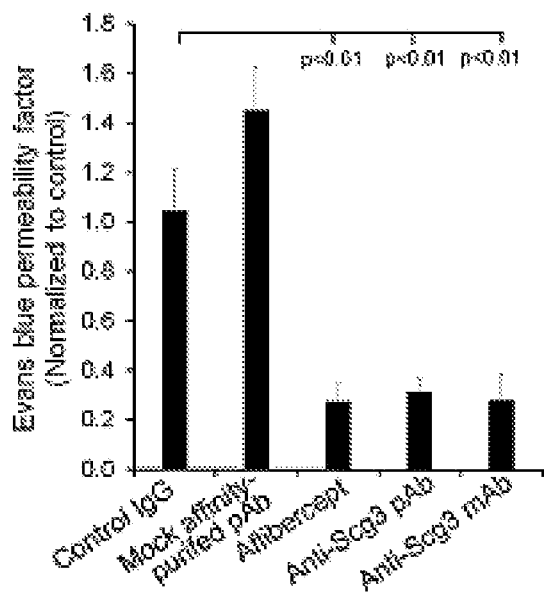
FIGS. 3A to 3F depict anti-Scg3 therapy of diabetic retinopathy.

Anti-Scg3 therapy alleviated diabetic retinal vascular leakage. Given the pathogenic role of angiogenic factors in DR, DR-high Scg3 was evaluated as a target for anti-angiogenesis therapy to alleviate diabetic retinal vascular leakage. Affinity-purified anti-Scg3 polyclonal antibody (pAb) was capable of blocking Scg3-induced proliferation of HRMVECs (FIG. 1B), but anti-Scg3 pAb alone had no effect on endothelial proliferation. The neutralizing activity of the pAb was independently confirmed by spheroid sprouting assay (FIG. 1F). Importantly, intravitreal injection of anti-Scg3 therapy significantly reduced retinal vascular leakage in STZ-induced diabetic mice with a similar therapeutic efficacy as aflibercept (FIG. 3A). As a control, mock affinity-purified pAb against an irrelevant antigen had no inhibition on diabetic retinal vascular leakage.

Figure 3B:
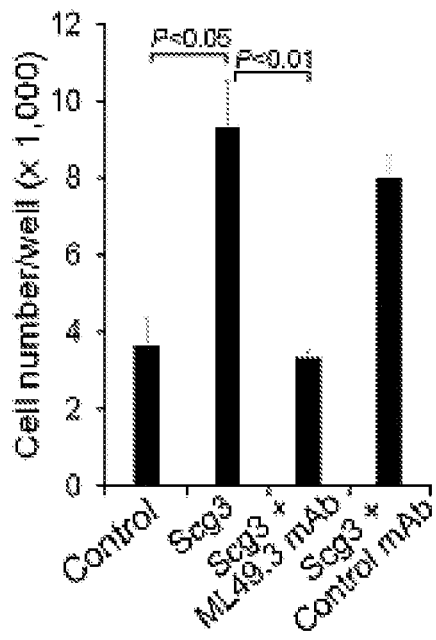
Figure 3C:
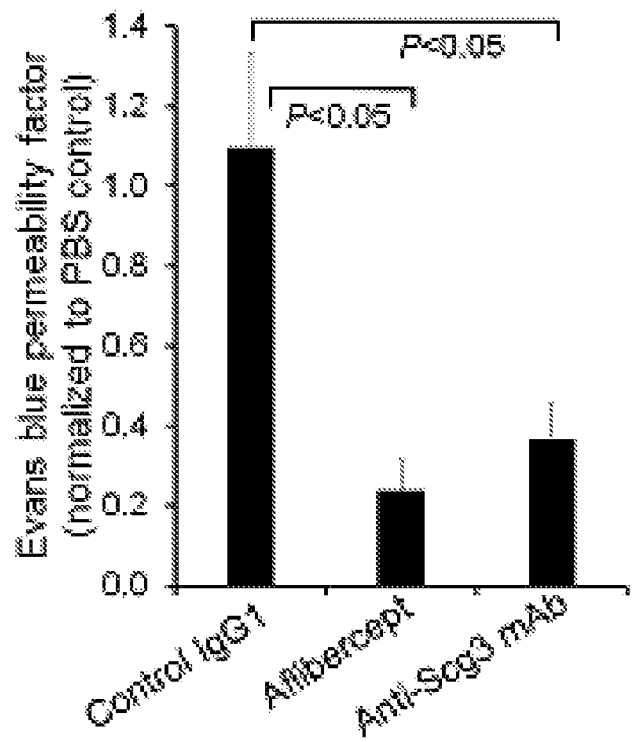
Figure 3D:
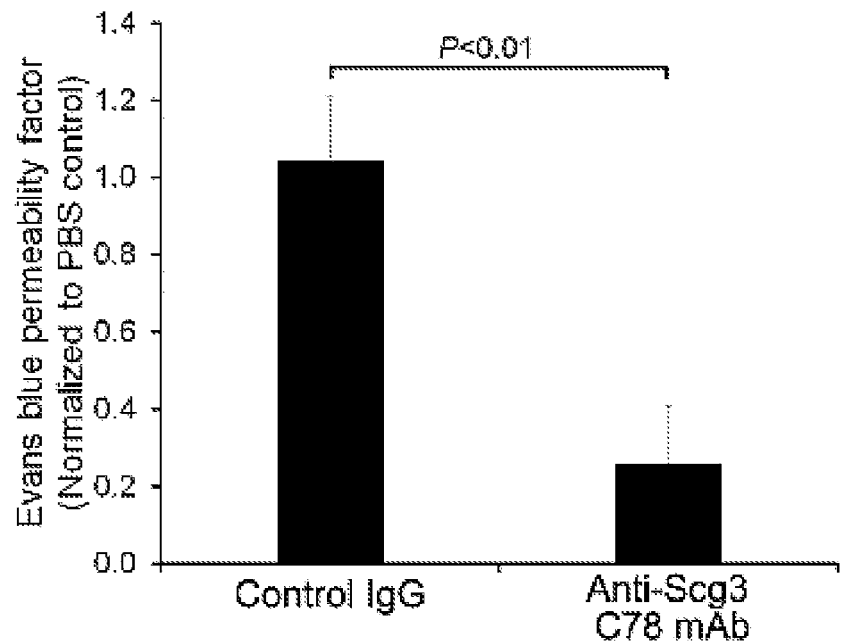

Independent validation of anti-Scg3 therapy. Despite affinity purification and various controls, however, pAb may non-specifically recognize other proteins with off-target effects. Unlike pAb, monoclonal antibodies (mAbs) minimally cross-react with other proteins and are well recognized as selective reagents for target validation as well as therapy. Anti-Scg3 mAbs (Clone 49 and Clone 78) were developed, which recognized both human and mouse Scg3. Intravitreal injection of Scg3-neutralizing mAb Clone 49 or Clone 78 alleviated retinal vascular leakage in STZ-induced diabetic mice (FIG. 3A and FIG. 3D) and neutralized Scg3-induced proliferation of HRMVECs (FIG. 3B), demonstrating that Scg3 is a bona fide target for anti-angiogenic therapy of DR.

Ins2$^{Akita}$ mice with a mutation in insulin 2 gene spontaneously develop type 1 diabetes (Wang et al. *J Clin Invest.* 1999; 103(1):27-37) and were used to independently verify the therapeutic efficacy of anti-Scg3 mAb. The mice develop retinal vascular leakage at 6 months of age. Intravitreal injection of anti-Scg3 mAb significantly inhibited retinal leakage in Ins2$^{Akita}$ mice with a similar efficacy to aflibercept (FIG. 3C), further corroborating Scg3 as a target for DR therapy.

Figure 3E:
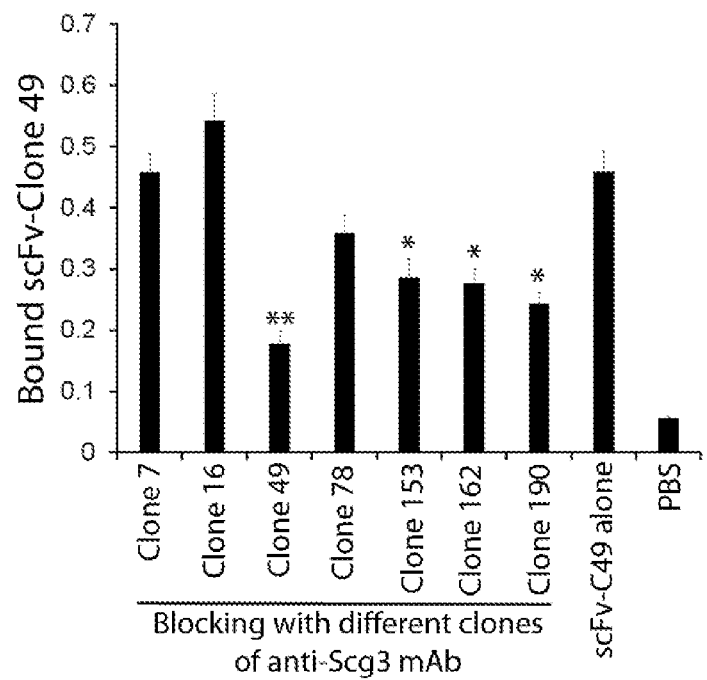
Figure 3F:
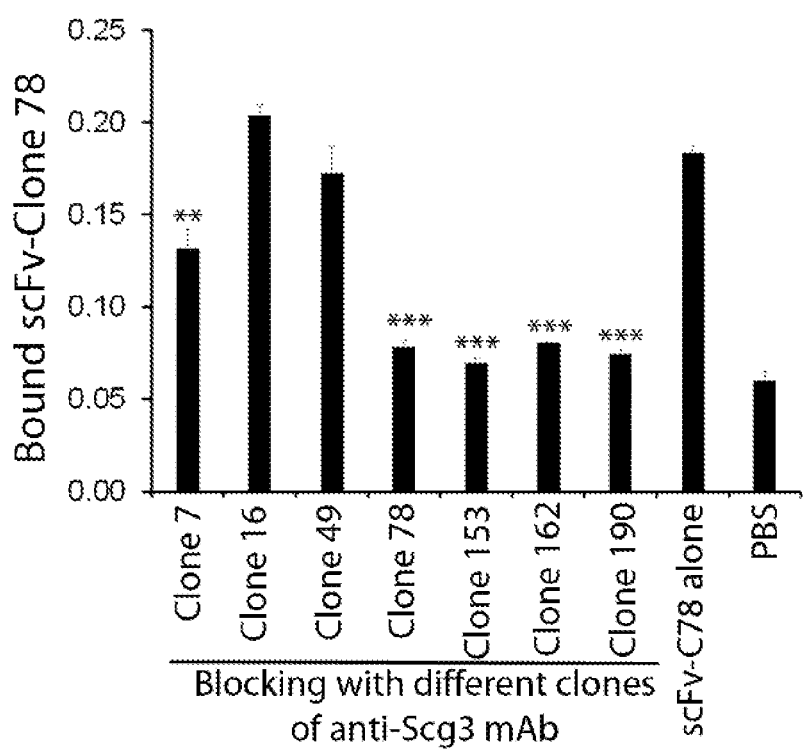
Figure 4A:
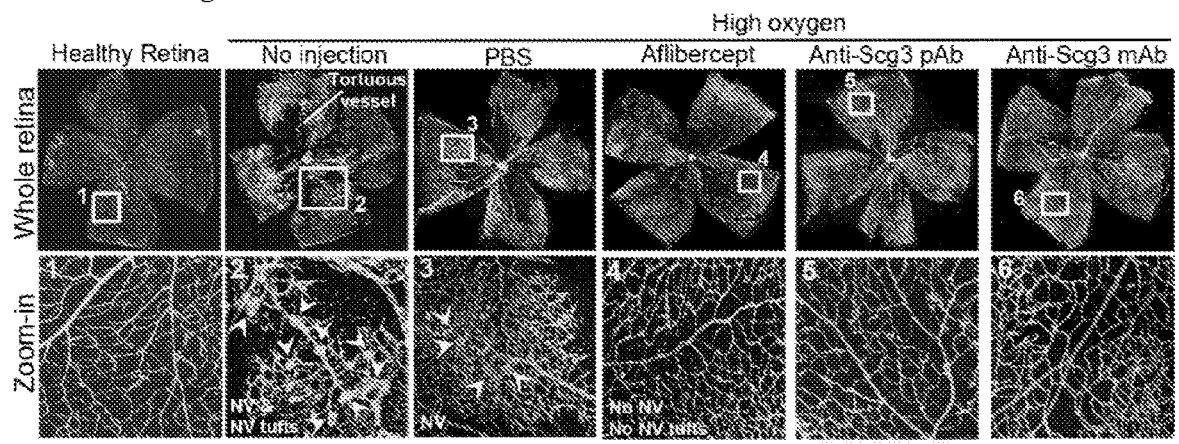
FIGS. 4A to 4D depict anti-Scg3 therapy of OIR.
Figure 4B:
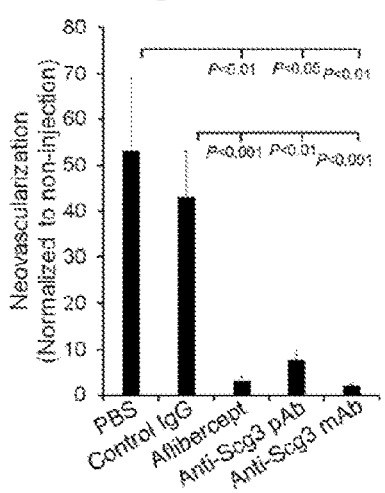
Figure 4C:
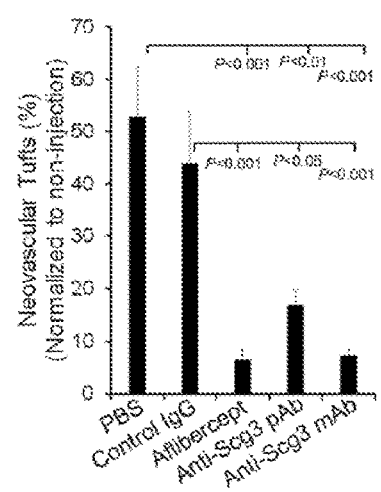
Figure 4D:
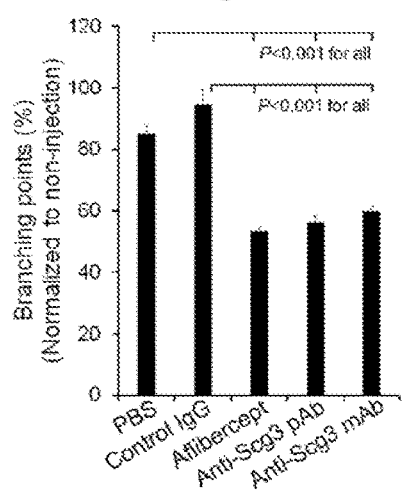

Competitive binding to Scg3 was evaluated for Clone 49 and the other anti-Scg3 mAbs described in Table 1. Anti-Scg3 scFv Clone 49 (FIG. 3D) and Clone 78 (FIG. 3E) were expressed and purified. Their binding activity to Scg3 pre-immobilized on ELISA plates was quantified in the presence or absence of excessive anti-Scg3 Clone 7, Clone 16, Clone 49, Clone 78, Clone 153, Clone 162 and Clone 190 mAb to block scFv binding. Bound scFv was detected by ELISA assay. Binding assays were also performed using an Octet RED96 system (Pall ForteBio), as described in Estep et al., *MAbs* 2013; 5:270-278. Both types of binding assays showed that Clone 48 and Clone 78 bound to Scg3, but did not block each other, indicating that they bind different epitopes on Scg3. Both binding assays also demonstrated that Clone 153, Clone 162, and Clone 190 competed with Clone 78 for binding to Scg3, indicating a shared epitope among those mAbs.

Anti-Scg3 therapy of retinal angiogenesis. In contrast to diabetic patients who may develop PDR 10 to 20 years after the disease onset, diabetic rodents do not progress toward PDR, probably due to their relatively short lifespan. Oxygen-induced retinopathy (OIR) is an animal model of retinopathy of prematurity (ROP) and has been widely used as a surrogate model of proliferative retinopathy with retinal neovascularization (Stahl et al. *Invest Ophthalmol Vis Sci.* 2010; 51(6):2813-26; Connor et al. *Nat Protoc.* 2009; 4(11):

1565-73). The ability of anti-Scg3 therapy to prevent retinal neovascularization induced by OIR was assessed. Intravitreal injection of Scg3-neutralizing pAb ameliorated OIR-induced pathological neovascularization characterized by neovascular tufts and tortuous blood vessels. The quantification of vessel density, neovascular tufts and vessel branching points indicated that anti-Scg3 significantly inhibited OIR-induced neovascularization (FIG. 4A-4D). Similar therapeutic effects were also observed for aflibercept. These data demonstrate the therapeutic potential of anti-Scg3 for PDR patients, as well as ROP patients.

Discussion

Comparative ligandomics. The reliability of quantitative ligandomics to globally quantify ligand binding activity is discussed further in U.S. patent application Ser. No. 14/708,073, incorporated herein by reference. Comparative ligandomics was applied to systematically delineate disease-associated ligands with altered binding in the disease state. The successful demonstration of anti-Scg3 therapy for DR corroborated the utility of this approach. Taken together, these findings indicated that profiling the binding activity of endogenous ligands by comparative ligandomics is a powerful approach to systematically identify disease-associated ligands and can be extended to define the pathogenic contributions and therapeutic potential of disease-associated ligands, which may accelerate or delay disease pathogenesis depending on the context.

The major advantage of comparative ligandomics was demonstrated by DR-high Scg3. Disease-high ligands with relatively low binding activities in healthy cells are likely to be overlooked by conventional ligand screening approaches. As a result, Scg3 has never been reported as an angiogenic factor. Comparative ligandomic analysis can efficiently screen for disease-high ligands, followed by additional functional analyses in healthy and diseased cells or conditions.

Scg3 was identified as a DR-high ligand by ligandomics with 1,731 and 0 copies in diabetic and healthy retina, respectively (Table 2). These numbers will increase or decrease in parallel based on the total number of sequences analyzed by NGS. Therefore, reduced Scg3 binding to healthy retinal endothelium likely does not indicate the absolute absence of Scg3 receptor(s), but rather suggests its relatively low expression. Indeed, weak Scg3 angiogenic activity, albeit not statistically significant, was detected by in vivo angiogenesis assay in healthy cornea (Scg3 vs. PBS). Furthermore, Scg3 was capable of stimulating HUVECs at a relatively high dose, suggesting that Scg3 regulation of non-diabetic ECs can be detected by other functional assays.

Scg3 as a DR-associated angiogenic ligand. The functional role of Scg3 is poorly defined and has been largely characterized as a regulator for secretory granule biogenesis and hormone peptide secretion in endocrine and neuroendocrine cells (Hosaka et al. *Endocrine journal*. 2010; 57(4): 275-86). However, secreted Scg3 has never been described as a ligand to extrinsically regulate any cells. This example discovered Scg3 was a DR-associated angiogenic factor. Anti-Scg3 therapy of diabetic retinal leakage and OIR-induced retinal neovascularization indicated that Scg3 was a pathogenic ligand in these two disease models and a potential target for anti-angiogenic therapy of DME and PDR. Owing to limited therapeutic options, DME patients with a poor response to one anti-VEGF drug are often switched to another VEGF inhibitor, despite their similar mechanisms of action. Developing anti-angiogenic therapy targeting different signaling pathways could facilitate alternative or combination therapy of anti-VEGF-resistant DR.

Based on the distinct angiogenic activity patterns, it was demonstrated that Scg3 and VEGF have different receptor signaling pathways. VEGF has three receptors, VEGFR1, 2 and 3. The first two receptors play a key role in the pathogenesis of ocular neovascularization (Robinson et al. *J Cell Sci*. 2001; 114(Pt 5):853-65), whereas VEGFR3 involves in lymphangiogenesis (Kaipainen et al. *Proc Natl Acad Sci USA*. 1995; 92(8):3566-70). The experiments independently verified that Scg3 did not bind to VEGFR1 and 2 by protein pulldown and ELISA. Because some angiogenic factors may induce VEGF expression (Matei et al. *Cancer Biol Ther*. 2007; 6(12):1951-9), it was further confirmed that Scg3 did not upregulate VEGF expression, or vice versa. These data indicated that Scg3 and VEGF have different spectra of angiogenic activity, supporting alternative or combination therapy for DR with their inhibitors.

Other potential advantages of anti-Scg3 therapy are minimal side effects and flexible administration routes. In contrast to embryonic lethality of mice with the deletion of a single VEGF allele (Ferrara et al. *Nature*. 1996; 380(6573): 439-42), mice with homozygous deletion of Scg3 gene (i.e., 1B1075 gene, equivalent of 100% Scg3 blockade) display a normal phenotype (Kingsley et al. *EMBO J*. 1990; 9(2):395-9), which suggests that anti-Scg3 therapy may have minimal side effects. A potential clinical application of anti-angiogenic therapy is the prevention of DME/PDR before the disease onset (Jeganathan VS. *Current pharmaceutical biotechnology*. 2011; 12(3):369-72.). However, owing to intravitreal injection-related and unrelated adverse effects, anti-VEGF therapy has a limited benefit-risk ratio for the prevention of DME/PDR. Systemic anti-Scg3 therapy with minimal side effects can improve the ratio and open the opportunity for the prevention of PDR/DME. Similar to LUCENTIS, Scg3-neutralizing mAb can be humanized for bench-to-bedside translation of anti-Scg3 therapy.

VEGF is crucial to vascular and retinal development at embryonic and neonatal stages. Mice with a homozygous deletion of either VEGF receptor 1 or 2 die in the uterus (Fong et al., *Nature*. 1995; 376:66-70; Shalaby et al., *Nature*. 1995; 376:62-66). Similarly, mice with the deletion of a single VEGF allele are embryonically lethal (Ferrara et al., *Nature*. 1996; 380:439-442). In all VEGF or VEGFR knock-out mice, premature death was attributed to severe defects in vasculogenesis, which could in turn affect embryogenesis. Anti-VEGF therapy of ROP in preterm infants has been associated with adverse side effects (Beharry et al., *Semin Perinatol*. 2016; 40:189-202; Lepore et al., *Ophthalmology*. 2014; 121:2212-2219). Due to the uncertainty in efficacy and safety (Sanker et al., *Cohrane Database Syst. Rev.* 2016; 2:CD009734), VEGF inhibitors have not been approved for ROP therapy. This example established that anti-Scg3 therapy has high efficacy for OIR. The high disease selectivity of Scg3 indicates that anti-Scg3 therapy may have minimal side effects on normal vessels. This notion is supported by the reported normal phenotype of mice with homozygous deletion of Scg3 gene (i.e., 1B1075 gene, equivalent of 100% Scg3 blockade) (Kingsley et al., *EMBO J*. 1990; 9:395-399), suggesting minimal adverse effects on vasculogenesis and embryogenesis. The results in FIG. 4 demonstrate that anti-Scg3 antibodies are promising drug therapy for ROP with high efficacy and safety.

In summary, high-throughput screening by comparative ligandomics was performed to systematically identify disease-associated ligands. Scg3 was characterized as a unique angiogenic factor that preferentially induced angiogenesis in diabetic, but not healthy, vasculature and a promising target for anti-angiogenic therapy of DME, PDR, and ROP. Anti- Scg3 antibodies significantly alleviated OIR-induced pathological retinal neovascularization, indicating that anti-Scg3 therapy could treat DME and PDR, as well as become the first drug therapy for ROP with high efficacy and safety.

Example 2

Anti-Scg3 Therapy for CNV

Materials and Methods

Antibodies. Affinity-purified anti-Scg3 pAb was obtained from Proteintech (Rosemont, Ill., USA). Anti-Scg3 mAb (Clone 49 and Clone 78, mouse IgG1) were generated and purified from serum-free hybridoma-conditioned medium using protein G columns (Kim et al. *Clin Immunol.* 2011; 138(1):60-6). All antibodies were washed three times with phosphate-buffered saline (PBS) in Amicon centrifugal filter units (10 kDa cutoff, Millipore, Billerica, Mass., USA).

Cell Cultures. Human umbilical vein endothelial cells (HUVECs) were previously described (LeBlanc et al. *PLoS One.* 2015; 10(5):e0127904). Human retinal microvascular endothelial cells (HRMVECs) and complete classic medium kit with serum and CultureBoost were from Cell Systems (Kirkland, Wash.) (LeBlanc et al. *Mol Vis.* 2016; 22:374-86). Human VEGF165 and anti-VEGF antibody were from R&D Systems (Minneapolis, Minn.). Aflibercept was manufactured by Regeneron Pharmaceuticals (Tarrytown, N.Y.). HRMVECs at 4 to 8 passages were cultured with Scg3 (Sino Biological, Beijing, China) or medium control in the presence or absence of anti-Scg3 mAb in 96-well plates as described (LeBlanc et al. *PLoS One.* 2015; 10(5):e0127904). Cells in each well were collected by trypsin digestion at 48 h and quantified.

Spheroid sprouting assay. The assay was performed with HUVECs as described (LeBlanc et al. *PLoS One.* 2015; 10(5):e0127904). Briefly, methocel solution was prepared by dissolving methylcellulose (Sigma, St. Louis, Mo.) in EBM-2 medium (Lonza, Allendale, N.J.) at 1.2% (w/v) and centrifuged at 5,000×g for 2 h at 4° C. to clear debris. Cells at 80% confluence were harvested, counted, resuspended in EBM-2 medium containing 20% methocel and 10% fetal bovine serum (FBS), seeded at 750 cells/well in non-adhesive 96-well round-bottomed plates and cultured for 24 h. Spheroids were harvested, resuspended in EBM-2 medium containing fibrinogen (2.5 mg/ml) and aprotinin (0.05 mg/ml), and seeded in 24-well plates (~50 spheroids/ml/well). Clotting was induced by adding thrombin (12 units/ml) to each well. The spheroid-embedded fibrin gel was allowed to clot for 5 min at room temperature and then 20 min at 37° C. The fibrin gel was incubated with Scg3, VEGF or PBS in the basal medium containing 0.05 mg/ml aprotinin for 48 h. Photographs were taken using a phase contrast microscope, and average sprout lengths were quantified using ImageJ software (NIH).

Src activation. Src activation was detected as described (LeBlanc et al. *PLoS One.* 2015; 10(5):e0127904). HRMVECs were incubated overnight in EBM-2 medium supplemented with 0.2% FBS to reduce the effect of other growth factors. Cells were incubated with Scg3 or PBS in EBM-2 medium with or without anti-Scg3 mAb for 10 min in 37° C., lysed and analyzed by Western blot using antibody against phosphorylated Src (P-Src), Src or β-actin (Santa Cruz Biotechnology, Dallas, Tex.). Western blot signals were digitalized.

Scg3 and VEGF expression. HRMVECs were plated in 6-well plates and incubated with Scg3, VEGF or PBS in EBM-2 medium supplemented with 2% FBS for 48 h. After washing, cells were collected and analyzed by Western blot using anti-Scg3 mAb and anti-VEGF antibody. Western blot signals were digitalized.

Therapy of laser-induced CNV. C57BL/6 mice (6-7 weeks old, Jackson Laboratory, Bar Harbor, Me.) were subjected to laser photocoagulation (Argon laser, 532 nm, 100 mW, 100 ms, 100 μm, 4 spots/retina) to induce CNV on Day 0, as previously described (LeBlanc et al. *Mol Vis.* 2016; 22:374-86). Lesions with choroidal hemorrhage and linear or fused lesions were excluded as described (Poor et al. *Invest Ophthalmol Vis Sci.* 2014; 55(10):6525-34). On Day 3, anti-Scg3 pAb, control IgG, anti-Scg3 Clone 49 mAb (0.36 μg/1 μl/eye), aflibercept (2 μg/1 μl/eye) or PBS was intravitreally injected. Aflibercept at 2 μg/eye in mice is equivalent to 2 mg/eye in humans for nAMD therapy based on their relative vitreous volumes. On Day 7, mice received intraperitoneal injection of fluorescein sodium (0.1 ml, 2.5%) were analyzed for CNV leakage by fluorescein angiography 6 min post injection. The intensity of laser spots was quantified using ImageJ. On Day 8, eyecups of the retinal pigment epithelium (RPE)-choroid-sclera complex were isolated, stained with Alexa Fluor 488-isolectin B4, flat-mounted and analyzed by confocal microscopy (LeBlanc et al. *Mol Vis.* 2016; 22(374-86); Chan et al. *PLoS One.* 2015; 10(3):e0120587). CNV 3D volume was deconvoluted from z-stack images and quantified using Volocity software. The area size of the largest CNV z-stack image of each lesion and its fluorescence intensity were quantified to determine the CNV size and vessel density using ImageJ. Data are normalized against PBS control.

Therapy of Matrigel-induced CNV. Growth factor-reduced Matrigel (Corning, Corning, N.Y.) was diluted 1:4 with PBS and injected into the subretinal space of C57BL/6 mice (6-7 weeks old, 0.8 μl/retina) on Day 0, as described (Cao et al. *Invest Ophthalmol Vis Sci.* 2010; 51(11):6009-17). Anti-Scg3 pAb, rabbit control IgG, anti-Scg3 mAb, mouse control IgG1 (anti-c-Myc, Clone 9E10) (Developmental Studies Hybridoma Bank, Iowa City, Iowa), aflibercept or PBS was subcutaneously injected on Day 0, 2 and 4. To avoid human bias, reagents were coded for blinded study. On Day 7, fluorescein angiography was performed to analyze CNV leakage as above.

Statistical analysis. Data were expressed as mean±SEM and analyzed by one-way ANOVA test. Differences with $P<0.05$ were considered significant.

Results

Figure 1I:
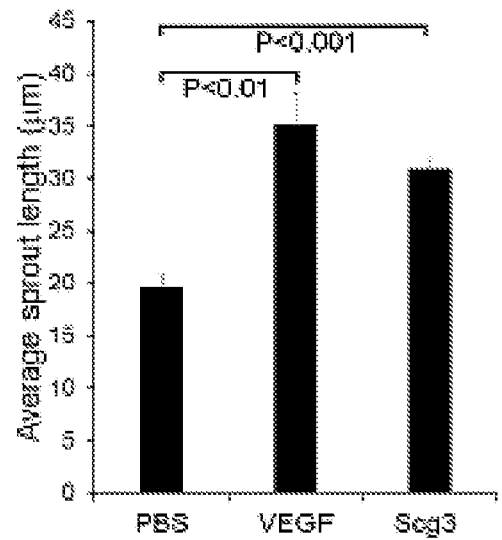

In vitro characterizations of Scg3 as a novel angiogenic factor. A 3D endothelial spheroid sprouting assay was performed to characterize the angiogenic activity of Scg3 in vitro. The results showed that Scg3 significantly stimulated the sprouting of HUVECs ($P<0.001$, FIG. 1I). As a positive control, VEGF induced similar endothelial sprouting ($P<0.01$), further supporting that Scg3 is an angiogenic factor.

Figure 5A:
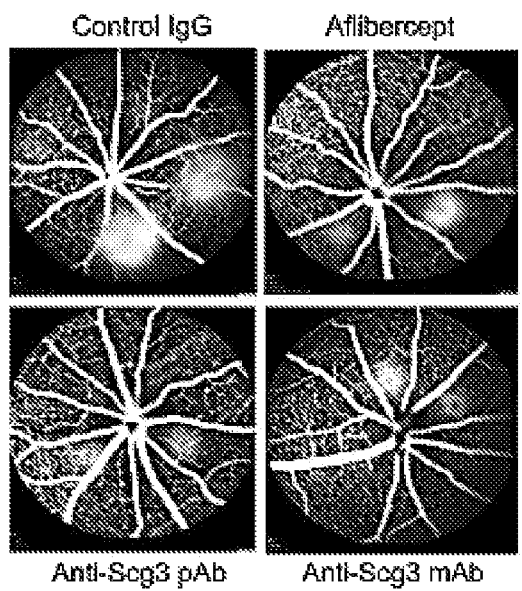
FIGS. 5A to 5E depict anti-Scg3 therapy of laser-induced CNV leakage. Mice were treated with laser photocoagulation on Day 0. PBS, control rabbit IgG (0.36 μg/μL/eye), aflibercept (2 μg/μL/eye), anti-Scg3 pAb (0.36 μg/μL/eye) or anti-Scg3 mAb (Clone 49) (0.36 μg/μL/eye) was intravitreally injected on Day 3.
Figure 5B:
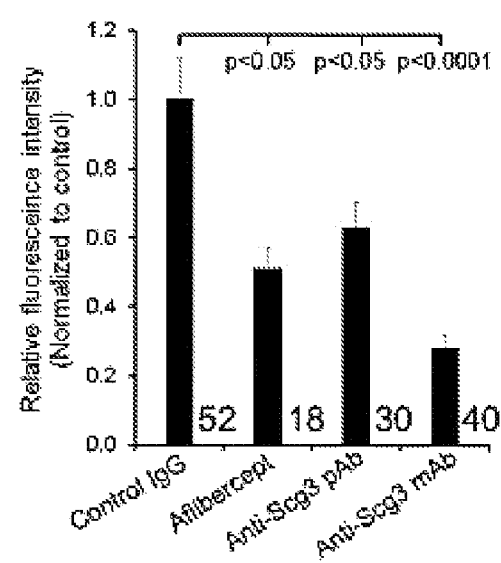
Figure 5C:
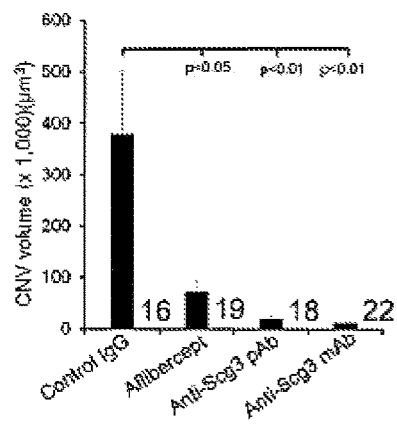
Figure 5D:
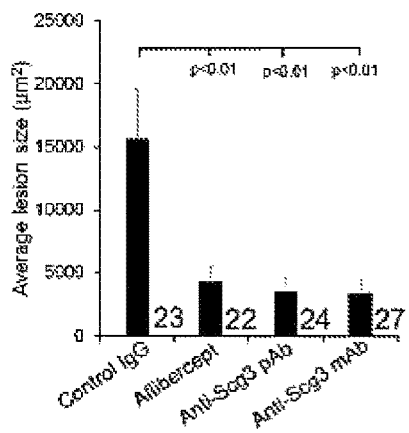
Figure 5E:
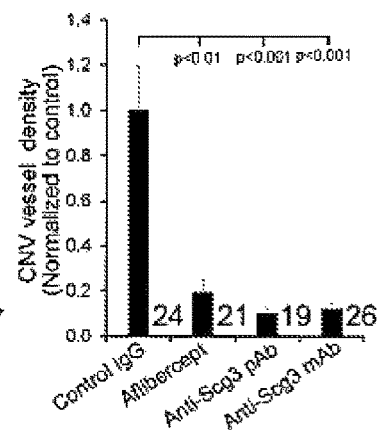

Anti-Scg3 therapy of laser-induced CNV with neutralizing pAb. To investigate possible contribution of Scg3 to CNV pathogenesis, the capacity of anti-Scg3 pAb to alleviate CNV in mice was analyzed. CNV in mice was induced by laser photocoagulation. Anti-Scg3 pAb, control IgG (0.36 μg/eye) or aflibercept (2 μg/eye) was intravitreally injected 3 days post photocoagulation. Fluorescein angiography on Day 7 showed that anti-Scg3 pAb significantly reduced CNV vessel leakage with a similar efficacy to aflibercept ($P<0.05$, FIG. 5A and FIG. 5B). CNV vessels in the eyecups were labeled with Alexa Fluor 488-isolectin B4 and analyzed by confocal microscopy. Anti-Scg3 pAb markedly reduced the size of CNV. Quantification of CNV 3D volume, lesion area and vessel density revealed that anti-Scg3 pAb significantly inhibited CNV with a similar efficacy to aflibercept (FIG. 5D to FIG. 5E).

Figure 6A:
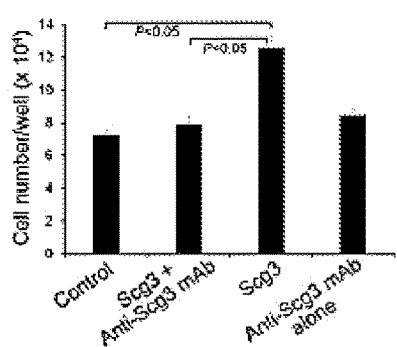
FIGS. 6A to 6C depict neutralization of Scg3 functional activity by anti-Scg3 mAb.
Figure 6B:
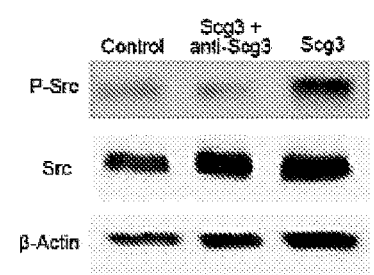
Figure 6C:
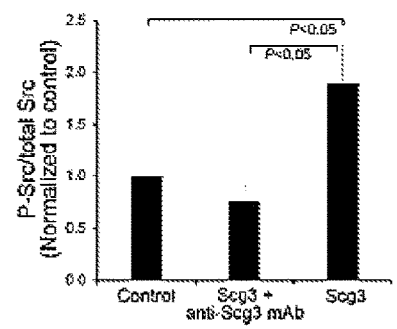

Anti-Scg3 therapy of laser-induced CNV with neutralizing mAb. Despite affinity purification, anti-Scg3 pAb recognizing multiple epitopes may non-specifically bind to other proteins with off-target effects. Monoclonal antibodies minimally cross-react with other proteins and therefore are well-recognized as selective reagents for target validation as well as therapy. To characterize the neutralizing activity of anti-Scg3 Clone 49 mAb, it was demonstrated that Scg3 significantly induced the proliferation of HRMVECs (P<0.05) and that the mAb inhibited Scg3-induced proliferation (P<0.05, FIG. 6A). These results confirmed that Scg3 is an angiogenic factor that promotes the growth of endothelial cells and that Clone 49 mAb is a Scg3-neutralizing antibody. Furthermore, signaling studies revealed that Scg3 significantly stimulated the phosphorylation of Src kinase in HRMVECs (P<0.05) and that Clone 49 mAb blocked Scg3-induced Src activation (P<0.05, FIG. 6B and FIG. 6C). The data using Clone 49 mAb confirmed the therapeutic activity of anti-Scg3 pAb, demonstrating that Scg3 plays an important role in CNV pathogenesis and is a promising target for anti-angiogenic therapy of CNV.

Figure 7A:
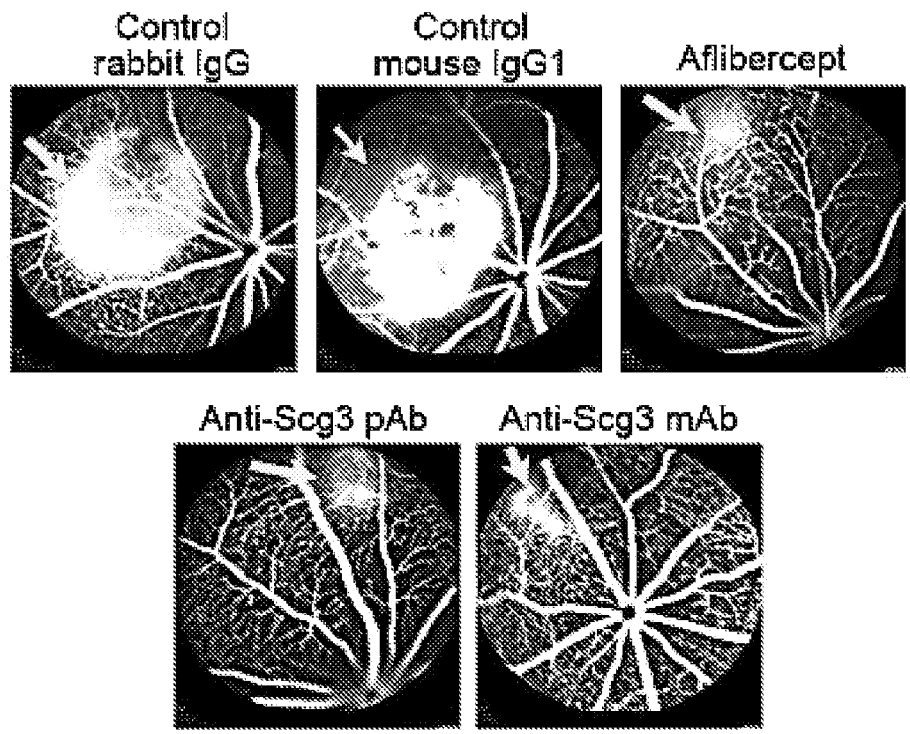
FIGS. 7A to 7D depict anti-Scg3 therapy of Matrigel-induced CNV.
Figure 7B:
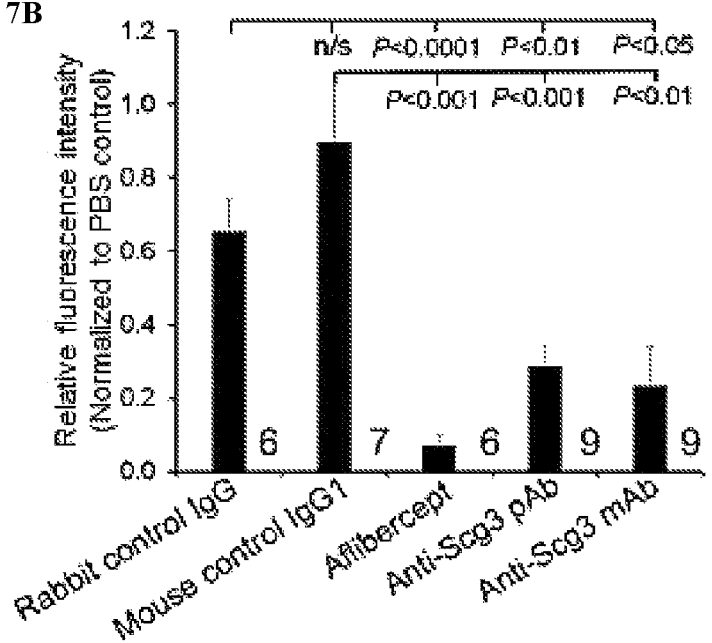
Figure 7C:
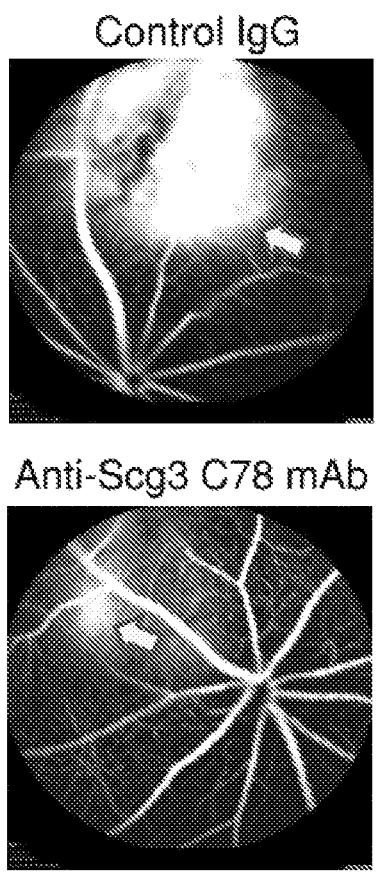
Figure 7D:
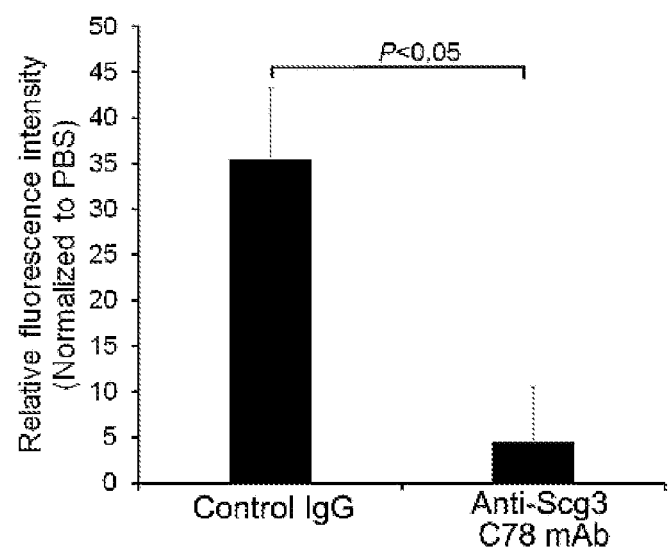

Anti-Scg3 therapy of Matrigel-induced CNV. To validate the pathogenic role of Scg3, an alternative mouse model of CNV was generated by injecting Matrigel (0.8 µl/retina) into the subretinal space to induce CNV, as described (Cao et al. *Invest Ophthalmol Vis Sci.* 2010; 51(11):6009-17). To circumvent the side effects of intravitreal injection, a proof-of-concept systemic anti-Scg3 therapy was investigated in this CNV model. Anti-Scg3 pAb, Clone 49 or Clone 78 mAb, control rabbit IgG, mouse IgG1 (25 µg/Kg body weight), aflibercept (250 g/Kg) or PBS was subcutaneously injected on Day 0, 2 and 4. Fluorescein angiography showed that anti-Scg3 pAb significantly prevented the onset of Matrigel-induced CNV (P<0.01, versus rabbit control IgG) (FIG. 7A and FIG. 7B). The results were independently verified with Clone 49 mAb (P<0.01, versus control mouse IgG1) (FIG. 7A and FIG. 7B) and with Clone 78 mAb (P<0.05, versus control IgG) (FIG. 7C and FIG. 7D). As a positive control, aflibercept also significantly inhibited Matrigel-induced CNV (FIG. 7B).

Cross-regulation of Scg3 and VEGF expression. Many angiogenic factors, such as platelet-derived growth factor (PDGF), fibroblast growth factor 2 (FGF-2) and epidermal growth factor (EGF), can upregulate VEGF expression (Wang et al. *Cancer research.* 1999; 59(7):1464-72; Seghezzi et al. *J Cell Biol.* 1998; 141(7):1659-73; Maity et al. *Cancer research.* 2000; 60(20):5879-86). Thus, they may indirectly promote angiogenesis through VEGF. To investigate this possibility, the effect of Scg3 on VEGF expression in HRMVECs was analyzed. The results showed that Scg3 did not upregulate VEGF expression, or vice versa (FIG. 8A to 8C). As a positive control, VEGF significantly promoted its own expression (P<0.05), as previously reported (Kweider et al. *J Biol Chem.* 2011; 286(50):42863-72). These results indicated that Scg3 and VEGF cannot regulate the expression of each other.

Discussion

This study characterized Scg3 as an angiogenic factor in CNV and a potential target for nAMD therapy. Compared with other angiogenic factors, Scg3 is unique because of its disease association. Scg3 does not bind to or induce angiogenesis of normal vessels. Thus, anti-Scg3 therapy should have a relatively high selectivity to CNV vessels. Furthermore, mice with the genetic ablation of Scg3 (i.e., 1B1075 gene, equivalent to 100% Scg3 blockade) have a normal phenotype (37), suggesting that anti-Scg3 may have minimal side effects on normal vessels and other cells. Indeed, it was found that intravitreal injection of Scg3-neutralizing mAb at an excessively high doses had no retinal toxicity and that Clone 49 mAb in high concentrations induced no detectable apoptosis of HRMVECs using FITC-annexin V labeling (unpublished data). These findings open the opportunity for systemic anti-Scg3 therapy of CNV. The results in FIG. 7 demonstrated systemic anti-Scg3 therapy of Matrigel-induced CNV with high efficacy. Anti-Scg3 with flexible administration routes will circumvent intravitreal injection-related adverse effects in the eye. Although this example demonstrated systemic anti-Scg3 therapy of CNV via subcutaneous injection as a proof-of-concept, different options for systemic therapy, including different injection sites, slow release formulation and extended half-life with PEGylated antibody, could be explored to maximize efficacy.

Both anti-Scg3 mAb and aflibercept markedly ameliorated laser- or Matrigel-induced CNV with more than 50% inhibition. Moreover, mechanistic studies showed that both Scg3 and VEGF activated ERK1/2 kinase. A critical question was whether Scg3 and VEGF may share the same receptor pathways for the robust inhibition of CNV and activation of ERK1/2. It was found that Scg3 does not bind to VEGF receptors (VEGFRs). Moreover, VEGF, but not Scg3, activated Akt kinase and signal transducer and activator of transcription 3 (STAT3). This study further revealed that Scg3 could not upregulate VEGF expression, or vice versa (FIG. 8A). Taken together, these results indicated that Scg3 is an angiogenic factor with a VEGF-independent signaling mechanism, providing a molecular basis for alternative or combination therapy of nAMD with their inhibitors. Scg3 and VEGF could have different receptors that activate distinct intracellular signaling pathways, which eventually converge to some common signaling molecules (e.g., EKR1/2) to regulate angiogenesis. Combination therapy with the inhibitors of Scg3 could thus potentially synergistically or additively improve the efficacy of CNV therapy.

An unexplored area is preventive therapy for nAMD. For example, patients with AMD susceptible genes, smoking, drusen or CNV in unilateral eye are at a high risk to develop nAMD. Owing to the injection-related adverse effects, intravitreal anti-VEGF therapy has a relatively low benefit-risk ratio for nAMD prevention before CNV onset. Systemic anti-Scg3 therapy with minimal side effects could improve this ratio, thereby opening the opportunity to prevent nAMD in patients of high-risk group. Thus, Scg3 is a promising target for both treatment and prevention of nAMD.

Example 3

Anti-Scg3 Therapy for Cancer

Comparative ligandomics analysis revealed that Scg3 bound to retinoblastoma in mice with 198 copies and normal retina with zero copy (FIG. 9A). Human MDA-MB-231 breast cancer cells ($2 \times 10^6$ cells/mouse) were implanted in a lateral mammary pad of immunodeficient NSG mice. After the tumor grew to the size of ~160 mm$^3$, mice were treated with anti-Scg3 mAb Clone 49 or control mouse IgG1 (5 mg/Kg body weight) through intraperitoneal injection. Tumor size was quantified before the next treatment with a total of 4 treatments.

Figure 9B:
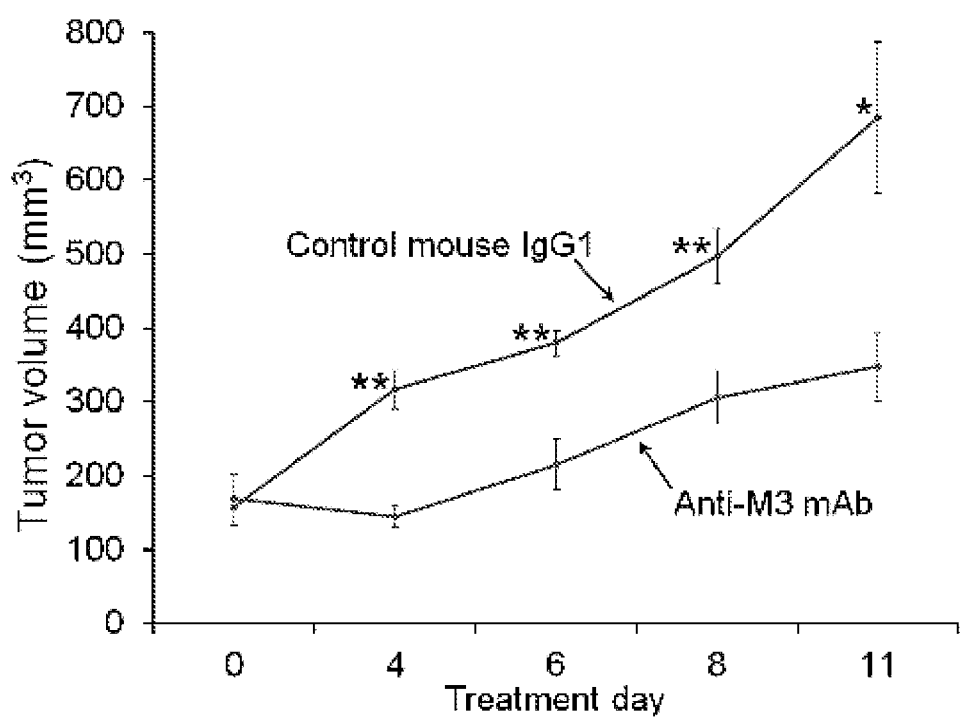

Animals treated with anti-Scg3 antibody exhibited significantly smaller tumor volumes compared to mice treated with control mouse IgG (FIG. 9B). The tumor growth was significantly reduced after the first treatment with anti-Scg3 mAb when compared with the tumors treated with control IgG. Additional treatments with anti-Scg3 mAb significantly suppressed tumor growth at all timepoints measured. No clinical signs of side effects, such as body weight loss, appetite loss, ruffled fur or dyspnea, were observed, demonstrating that anti-Scg3 mAb had minimal side effects.

The foregoing Examples demonstrate that Scg3 has minimal binding and angiogenic activity in normal vessels, but markedly upregulates its binding and angiogenic activity in multiple vascular diseases. In contrast to VEGF that is critical to vascular and retinal development, Scg3 plays a minimal role in the normal vascular and retinal morphogenesis. Mice with homozygous deletion of the Scg3 gene were reported with normal phenotype (Kingsley et al. *EMBO J.* 1990; 9(2):395-9), whereas mice with the deletion of a single VEGF allele are embryonically lethal (Ferrara et al. *Nature.* 1996; 380(6573):439-42). Anti-Scg3 therapy, including anti-Scg3 mAbs, are effective for treating symptoms associated with DR, nAMD with CNV/PCV, ROP, and cancer, and provide a promising alternative to current anti-VEGF therapeutic options.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. An antibody or antigen-binding fragment thereof that binds secretogranin Ill, wherein the antibody or antigen-binding fragment comprises the following CDR sequences:
   (i) (a) CDR-H1 comprises SEQ ID NO: 3; (b) CDR-H2 comprises SEQ ID NO: 4; (c) CDR-H3 comprises SEQ ID NO: 5; (d) CDR-L1 comprises SEQ ID NO: 6; (e) CDR-L2 comprises SEQ ID NO: 7; and (f) CDR-L3 comprises SEQ ID NO: 8;
   (ii) (a) CDR-H1 comprises SEQ ID NO: 11; (b) CDR-H2 comprises SEQ ID NO: 12; (c) CDR-H3 comprises SEQ ID NO: 13; (d) CDR-L1 comprises SEQ ID NO: 14; (e) CDR-L2 comprises SEQ ID NO: 15; and (f) CDR-L3 comprises SEQ ID NO: 16;
   (iii) (a) CDR-H1 comprises SEQ ID NO: 19; (b) CDR-H2 comprises SEQ ID NO: 20; (c) CDR-H3 comprises SEQ ID NO: 21; (d) CDR-L1 comprises SEQ ID NO: 22; (e) CDR-L2 comprises SEQ ID NO: 23; and (f) CDR-L3 comprises SEQ ID NO: 24;
   (iv) (a) CDR-H1 comprises SEQ ID NO: 27; (b) CDR-H2 comprises SEQ ID NO: 4; (c) CDR-H3 comprises SEQ ID NO: 28; (d) CDR-L1 comprises SEQ ID NO: 22; (e) CDR-L2 comprises SEQ ID NO: 29; and (f) CDR-L3 comprises SEQ ID NO: 24;
   (v) (a) CDR-H1 comprises SEQ ID NO: 27; (b) CDR-H2 comprises SEQ ID NO: 4; (c) CDR-H3 comprises SEQ ID NO: 28; (d) CDR-L1 comprises SEQ ID NO: 32; (e) CDR-L2 comprises SEQ ID NO: 29; and (f) CDR-L3 comprises SEQ ID NO: 24; or
   (vi) (a) CDR-H1 comprises SEQ ID NO: 3; (b) CDR-H2 comprises SEQ ID NO: 4; (c) CDR-H3 comprises SEQ ID NO: 28; (d) CDR-L1 comprises SEQ ID NO: 22; (e) CDR-L2 comprises SEQ ID NO: 29; and (f) CDR-L3 comprises SEQ ID NO: 24.

2. The antibody or antigen-binding fragment thereof of claim 1, comprising (i) a heavy chain variable region comprising SEQ ID NO: 1 and a light chain variable region comprising SEQ ID NO: 2; (ii) a heavy chain variable region comprising SEQ ID NO: 9 and a light chain variable region comprising SEQ ID NO: 10; (iii) a heavy chain variable region comprising SEQ ID NO: 17 and a light chain variable region comprising SEQ ID NO: 18; (iv) a heavy chain variable region comprising SEQ ID NO: 25 and a light chain variable region comprising SEQ ID NO: 26; (v) a heavy chain variable region comprising SEQ ID NO: 30 and a light chain variable region comprising SEQ ID NO: 31; (vi) a heavy chain variable region comprising SEQ ID NO: 38 and a light chain variable region comprising SEQ ID NO: 33; or (vii) a heavy chain variable region comprising SEQ ID NO: 34 and a light chain variable region comprising SEQ ID NO: 35.

3. The antibody or antigen-binding fragment thereof of claim 1, comprising (i) a heavy chain variable region comprising an amino acid sequence at least 90% identical to SEQ ID NO: 1 and a light chain variable region comprising an amino acid sequence at least 90% identical to SEQ ID NO: 2; (ii) a heavy chain variable region comprising an amino acid sequence at least 90% identical SEQ ID NO: 9 and a light chain variable region comprising an amino acid sequence at least 90% identical to SEQ ID NO: 10; (iii) a heavy chain variable region comprising an amino acid sequence at least 90% identical to SEQ ID NO: 17 and a light chain variable region comprising an amino acid sequence at least 90% identical to SEQ ID NO: 18; (iv) a heavy chain variable region comprising an amino acid sequence at least 90% identical to SEQ ID NO: 25 and a light chain variable region comprising an amino acid sequence at least 90% identical SEQ ID NO: 26; (v) a heavy chain variable region comprising an amino acid sequence at least 90% identical to SEQ ID NO: 30 and a light chain variable region comprising an amino acid sequence at least 90% identical SEQ ID NO: 31; (vi) a heavy chain variable region comprising an amino acid sequence at least 90% identical to SEQ ID NO: 38 and a light chain variable region comprising an amino acid sequence at least 90% identical SEQ ID NO: 33; or (vii) a heavy chain variable region comprising an amino acid sequence at least 90% identical to SEQ ID NO: 34 and a light chain variable region comprising an amino acid sequence at least 90% identical to SEQ ID NO: 35.

4. A pharmaceutical composition comprising the antibody or antigen-binding fragment thereof of claim 1 and a physiologically acceptable diluent, excipient or carrier.

5. A method of treating neovascular age-related macular degeneration, diabetic retinopathy, or retinopathy of prematurity in a subject in need thereof comprising administering a therapeutically effective amount of the antibody or antigen-binding fragment thereof of claim 1.

6. The method of claim 5, wherein the antibody or antigen-binding fragment thereof is administered in an amount effective to inhibit choroidal neovascularization or polypoidal choroidal vasculopathy.

7. The method of claim 5, wherein the antibody or antigen-binding fragment thereof is administered in an amount from about 5 µg/kg to about 400 mg/kg body weight of the subject.

8. The method of claim 5, wherein the antibody or antigen-binding fragment thereof is administered to the eye of the subject in an amount from about 0.05 mg to about 10 mg.

* * * * *

SEQUENCE LISTING

```
<160> NUMBER OF SEQ ID NOS: 38

<210> SEQ ID NO 1
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7 Monoclonal Antibody Heavy Chain (H)

<400> SEQUENCE: 1

Gln Val Lys Leu Glu Glu Ser Gly Pro Glu Leu Leu Lys Pro Gly Ala
1               5                   10                  15

Ser Val Lys Ile Ser Cys Lys Thr Ser Gly Tyr Ile Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly His Thr Asn Tyr Asn Gly Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Leu Ala Asp Gly Tyr Phe Phe Val Tyr Trp Gly Gln Gly Thr
            100                 105                 110

Pro Val Thr Val Ser Ala
        115

<210> SEQ ID NO 2
<211> LENGTH: 113
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7 Monoclonal Antibody Light Chain (L)

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30
```

```
Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                85                  90                  95

Glu Leu Pro Trp Thr Phe Gly Gly Gly Thr Lys Leu Glu Ile Lys Arg
            100                 105                 110

Ala

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7, CLONE 16, and CLONE 190 Monoclonal
      Antibody CDR-H1

<400> SEQUENCE: 3

Gly Tyr Ile Phe Ser Ser Ser Trp Met Asn
 1               5                  10

<210> SEQ ID NO 4
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7, CLONE 153, CLONE 162, and CLONE 190
      Monoclonal Antibody CDR-H2

<400> SEQUENCE: 4

Arg Ile Tyr Pro Gly Asp Gly His Thr Asn Tyr Asn Gly Lys Phe Lys
 1               5                  10                  15

Asp

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7 Monoclonal Antibody CDR-H3

<400> SEQUENCE: 5

Leu Ala Asp Gly Tyr Phe Phe Val Tyr
 1               5

<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

<223> OTHER INFORMATION: CLONE 7 Monoclonal Antibody CDR-L1

<400> SEQUENCE: 6

Arg Ala Ser Lys Ser Val Ser Thr Ser Gly Tyr Ser Tyr Met His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7 Monoclonal Antibody CDR-L2

<400> SEQUENCE: 7

Leu Ala Ser Asn Leu Glu Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 7 Monoclonal Antibody CDR-L3

<400> SEQUENCE: 8

Gln His Ser Arg Glu Leu Pro Trp Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody Heavy Chain (H)

<400> SEQUENCE: 9

Glu Val Lys Leu Glu Glu Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Asn Gly Pro Gly Thr Pro Trp Phe Ala Tyr Trp Gly Gln Gly
            100                 105                 110

Thr Leu Val Thr Val Ser Ala
        115

<210> SEQ ID NO 10
<211> LENGTH: 109

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody Light Chain (L)

<400> SEQUENCE: 10

Asp Ile Gln Met Thr Gln Ser Ser Tyr Leu Ser Val Ser Leu Gly
1               5                   10                  15

Gly Arg Val Thr Ile Thr Cys Lys Ala Ser Asp His Ile Asn Asn Trp
                20                  25                  30

Leu Thr Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys Arg Ala
            100                 105

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody CDR-H1

<400> SEQUENCE: 11

Gly Phe Asn Ile Lys Asp Thr Tyr Met His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody CDR-H2

<400> SEQUENCE: 12

Arg Ile Asp Pro Ala Asn Gly Asp Thr Lys Tyr Asp Pro Lys Phe Gln
1               5                   10                  15

Gly

<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody CDR-H3

<400> SEQUENCE: 13

Asn Gly Pro Gly Thr Pro Trp Phe Ala Tyr
```

<210> SEQ ID NO 14
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody CDR-L1

<400> SEQUENCE: 14

Lys Ala Ser Asp His Ile Asn Asn Trp Leu Thr
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody CDR-L2

<400> SEQUENCE: 15

Gly Ala Thr Ser Leu Glu Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 49 Monoclonal Antibody CDR-L3

<400> SEQUENCE: 16

Gln Gln Tyr Trp Ser Thr Pro Phe Thr
1               5

<210> SEQ ID NO 17
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78 Monoclonal Antibody Heavy Chain (H)

<400> SEQUENCE: 17

Glu Val Gln Leu Gln Gln Ser Gly Pro Glu Leu Leu Lys Pro Gly Ala
1               5                   10                  15

Ser Val Lys Ile Ser Cys Lys Thr Ser Gly Tyr Ile Phe Ser Ala Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly His Thr Asn Tyr Asn Gly Lys Ile
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys

```
                85                  90                  95

Ala Arg Ser Ala Asp Gly Tyr Phe Phe Val Asp Trp Gly Gln Gly Thr
                100                 105                 110

Leu Val Thr Val Ser Ala
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78 Monoclonal Antibody Light Chain (L)

<400> SEQUENCE: 18

Asp Ile Val Met Thr Gln Thr Pro Val Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Phe Lys Val Ser Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Pro Thr Phe Gly Gly Gly Thr Lys Leu Glu Ile Lys
                100                 105                 110

Arg Ala

<210> SEQ ID NO 19
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78 Monoclonal Antibody CDR-H1

<400> SEQUENCE: 19

Gly Tyr Ile Phe Ser Ala Ser Trp Met Asn
1               5                   10

<210> SEQ ID NO 20
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78 Monoclonal Antibody CDR-H2

<400> SEQUENCE: 20

Arg Ile Tyr Pro Gly Asp Gly His Thr Asn Tyr Asn Gly Lys Ile Lys
1               5                   10                  15

Asp
```

```
<210> SEQ ID NO 21
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78 Monoclonal Antibody CDR-H3

<400> SEQUENCE: 21

Ser Ala Asp Gly Tyr Phe Phe Val Asp
1               5

<210> SEQ ID NO 22
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78, CLONE 153, CLONE 16, and CLONE 190
      Monoclonal Antibody CDR-L1

<400> SEQUENCE: 22

Arg Ser Ser Gln Ser Ile Val His Ser Asn Gly Asn Thr Tyr Leu Glu
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78 Monoclonal Antibody CDR-L2

<400> SEQUENCE: 23

Lys Val Ser Lys Arg Phe Tyr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 78, CLONE 153, CLONE 162, CLONE 16, and
      CLONE 190 Monoclonal Antibody CDR-L3

<400> SEQUENCE: 24

Phe Gln Gly Ser His Val Pro Pro Thr
1               5

<210> SEQ ID NO 25
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 153 Monoclonal Antibody Heavy Chain (H)

<400> SEQUENCE: 25

Gly Arg Lys Leu Gln Glu Ser Gly Pro Glu Leu Leu Lys Pro Gly Ala
```

```
            1               5                  10                 15
Ser Val Lys Ile Ser Cys Lys Thr Ser Gly Tyr Ile Phe Ser Thr Ser
                20                  25                 30

Trp Met Asn Trp Val Lys Gln Arg Pro Gly Gln Gly Leu Glu Trp Ile
                35                  40                 45

Gly Arg Ile Tyr Pro Gly Asp Gly His Thr Asn Tyr Asn Gly Lys Phe
        50                  55                  60

Lys Asp Lys Ala Thr Leu Thr Ala Asp Lys Ser Ser Thr Ala Tyr
 65                 70                  75                 80

Met Gln Leu Ser Ser Leu Thr Ser Val Asp Ser Ala Val Tyr Phe Cys
                85                  90                 95

Ala Arg Ser Ala Asp Gly Tyr Phe Phe Val Tyr Trp Gly Gln Gly Thr
                    100                 105                110

Leu Val Thr Val Ser Ala
            115
```

<210> SEQ ID NO 26
<211> LENGTH: 114
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 153 Monoclonal Antibody Light Chain (L)

<400> SEQUENCE: 26

```
            1               5                  10                 15
Asp Ile Val Leu Thr Gln Thr Pro Leu Ser Leu Pro Val Ser Leu Gly
                20                  25                 30

Asp Gln Ala Ser Ile Ser Cys Arg Ser Ser Gln Ser Ile Val His Ser
                35                  40                 45

Asn Gly Asn Thr Tyr Leu Glu Trp Tyr Leu Gln Lys Pro Gly Gln Ser
        50                  55                  60

Pro Lys Leu Leu Ile Phe Lys Val Ser Lys Arg Phe Ser Gly Val Pro
 65                 70                  75                 80

Asp Arg Phe Ser Gly Ser Gly Ser Gly Thr Asp Phe Thr Leu Lys Ile
                85                  90                 95

Ser Arg Val Glu Ala Glu Asp Leu Gly Val Tyr His Cys Phe Gln Gly
                    100                 105                110

Ser His Val Pro Pro Thr Phe Gly Gly Thr Lys Leu Glu Ile Lys
Arg Ala
```

<210> SEQ ID NO 27
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 153 and CLONE 162 Monoclonal Antibody
    CDR-H1

<400> SEQUENCE: 27

```
            1               5                  10
Gly Tyr Ile Phe Ser Thr Ser Trp Met Asn
```

<210> SEQ ID NO 28
<211> LENGTH: 9

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 153, CLONE 162, CLONE 16, and CLONE 190
      Monoclonal Antibody CDR-H3

<400> SEQUENCE: 28

Ser Ala Asp Gly Tyr Phe Phe Val Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 153, CLONE 16, CLONE 16, and CLONE 190
      Monoclonal Antibody CDR-L2

<400> SEQUENCE: 29

Lys Val Ser Lys Arg Phe Ser
1               5

<210> SEQ ID NO 30
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 162 Monoclonal Antibody Heavy Chain (H)

<400> SEQUENCE: 30

Pro Gly Lys Ala Glu Glu Ser Gly Pro Glu Met Leu Lys Pro Gly Ala
1               5                   10                  15

Ser Val Lys Ile Ser Cys Lys Thr Ser Gly Tyr Ile Phe Ser Thr Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly His Thr Asn Tyr Asn Gly Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Ala Asp Ser Ala Val Tyr Phe Cys
                85                  90                  95

Ala Arg Ser Ala Asp Gly Tyr Phe Phe Val Tyr Trp Gly Gln Gly Thr
            100                 105                 110

Leu Val Thr Val Ser Ala
        115

<210> SEQ ID NO 31
<211> LENGTH: 114
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 162 Monoclonal Antibody Light Chain (L)
```

-continued

<400> SEQUENCE: 31

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Phe Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr His Cys Phe Gln Gly
                85                  90                  95

Ser His Val Pro Pro Thr Phe Gly Gly Gly Thr Lys Leu Glu Ile Lys
            100                 105                 110

Arg Ala

<210> SEQ ID NO 32
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 162 Monoclonal Antibody CDR-L1

<400> SEQUENCE: 32

Arg Ser Ser Gln Asn Ile Ile His Ser Asn Gly Asn Thr Tyr Leu Glu
1               5                   10                  15

<210> SEQ ID NO 33
<211> LENGTH: 114
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 16 Monoclonal Antibody Light Chain (L)

<400> SEQUENCE: 33

Asp Ile Val Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Phe Lys Val Ser Lys Arg Phe Ser Gly Val Pro
    50                  55                  60

Asp Arg Phe Ser Gly Ser Gly Leu Gly Thr Asp Phe Thr Leu Lys Ile
65                  70                  75                  80

Ser Arg Val Gly Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg Ala

<210> SEQ ID NO 34

```
<211> LENGTH: 118
<212> TYPE: PRT
<213> ORGANISM: Artificial Sequence
<220> FEATURE:
<223> OTHER INFORMATION: Synethetic Polypeptide
<220> FEATURE:
<221> NAME/KEY: MISC_FEATURE
<223> OTHER INFORMATION: CLONE 190 Monoclonal Antibody Heavy Chain (H)

<400> SEQUENCE: 34

Glu Val Lys Leu Glu Glu Ser Gly Pro Glu Leu Leu Lys Pro Gly Ala
1               5                   10                  15

Ser Val Lys Ile Ser Cys Lys Thr Ser Gly Tyr Ile Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly His Thr Asn Tyr Asn Gly Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Ala Asp Gly Tyr Phe Phe Val Tyr Trp Gly Gln Gly Thr
            100                 105                 110

Pro Val Thr Val Ser Ala
        115

<210> SEQ ID NO 35
<211> LENGTH: 114
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 190 Monoclonal Antibody Light Chain (L)

<400> SEQUENCE: 35

Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Phe Lys Val Ser Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gly Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg Ala

<210> SEQ ID NO 36
<211> LENGTH: 20
<212> TYPE: DNA
<213> ORGANISM: Artificial Sequence
<220> FEATURE:
<223> OTHER INFORMATION: Synthetic Primer
```

```
<400> SEQUENCE: 36
gcggttcagg ctcgcggccg                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic Primer

<400> SEQUENCE: 37
ccgctcccac taccctcgag                                              20

<210> SEQ ID NO 38
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: CLONE 16 Monoclonal Antibody Heavy Chain (H)

<400> SEQUENCE: 38

Glu Val Lys Leu Glu Gln Ser Gly Pro Glu Leu Leu Lys Pro Gly Ala
1               5                   10                  15

Ser Val Lys Ile Ser Cys Lys Thr Ser Gly Tyr Ile Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly His Thr Asn Tyr Asn Gly Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Ala Asp Gly Tyr Phe Phe Val Tyr Trp Gly Gln Gly Thr
            100                 105                 110

Pro Val Thr Val Ser Ala
            115
```